US006355788B1

(12) United States Patent
Conklin et al.

(10) Patent No.: US 6,355,788 B1
(45) Date of Patent: Mar. 12, 2002

(54) FOLLISTATIN-RELATED PROTEIN ZFSTA2

(75) Inventors: Darrell C. Conklin; Jeff L. Ellsworth, both of Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/412,554

(22) Filed: Oct. 5, 1999

Related U.S. Application Data

(60) Provisional application No. 60/104,431, filed on Oct. 15, 1998.

(51) Int. Cl.[7] ......................... C07H 21/04; C12P 21/06; C12P 21/04; C07K 16/00; A61K 28/00

(52) U.S. Cl. .................... 536/23.4; 536/23.5; 435/69.1; 435/69.7; 530/320; 530/324; 514/2

(58) Field of Search ............................... 536/23.5, 23.4; 435/69.1, 69.7; 530/320, 324; 514/2

(56) References Cited

FOREIGN PATENT DOCUMENTS

WO 93/16178 8/1993

OTHER PUBLICATIONS

Macke et al., GenBank accession No. W27213, May 8, 1996.*
Sambrook et al, Molecular Cloning, 2nd Edition, 1989, pp. 17.2–17.9.*
Zwijsen et al., *Eur. J. Biochem.* 225: 937–946, 1994.
Lane & Sage, *FASEB J.* 8: 163–173, 1994.
Hohenester et al., *EMBO J.* 16: 3778–3786, 1997.
Girard & Springer, *Immunity* 2: 113–123, 1995.
Mendis & Brown, *Brain Res.* 730: 95–106, 1996.
Bode & Huber, *Eur. J. Biochem.* 24: 433–451, 1992.
Mather et al., *P.S.E.B.M.* 215: 209–222, 1997.
Matzuk et al., *Nature* 374: 360–363, 1995.
Amthor et al., *Development Biol.* 178: 343–362, 1996.
Patthy & Nikolics, *TINS* 16: 76–81, 1993.
Inouye et al., *Biochem. Biophys. Res. Comm.* 179: 352–358, 1991.
Matzuk et al., *Nature* 374: 356–360, 1995.
Citron et al., *Nature Medicine 3*: 67–72, 1997.
Bork et al., *J. Mol. Biol.* 242: 309–320, 1994.
Adams et al., Nature 355: 632–4, 1992. Accession No. 274298.
Wilson, WashU–Merck EST Project, 1995. Accession No. 792530.
Incyte Clone Information Results, Incyte Pharmaceuticals 1995. Accession No. INC384371.
LifeSeq® Library Information Results, Incyte Pharmaceuticals, 1995.
Macke et al., Adult Human Retina cDNA, 1996. Accession No. W27213.
Kerlavage, TIGR EST, 1997. Accession No. AA350667.
LifeSeq® Library Information Results, Incyte Pharmaceuticals 1997, No. SKINNOT05.
Incyte Clone Information Results, Incyte Pharmaceuticals, 1998, Accession No. INC4291695.
Incyte Clone Information Results, Incyte Pharmaceuticals, 1998, Accession No. INC4023645.
LifeSeq® Library Information Results, Incyte Pharmaceuticals 1998, No. BRABDIR01.
LifeSeq® Library Information Results, Incyte Pharmaceuticals 1998, No. BRAXNOT02.

* cited by examiner

*Primary Examiner*—Yvonne Eyler
*Assistant Examiner*—Janet L. Andres
(74) *Attorney, Agent, or Firm*—Susan E. Lingenfelter

(57) ABSTRACT

The present invention relates to polynucleotide and polypeptide molecules for zfsta2, a novel member of the follistatin family. The polypeptides, and polynucleotides encoding them are useful for binding to members of the TGF-β family and mediating central nervous system, reproductive, hematopoietic and bone-related activities. The present invention also includes antibodies to the zfsta2 polypeptides.

1 Claim, No Drawings

SEQUENCE LISTING

```
<160> NUMBER OF SEQ ID NOS:  15

<210> SEQ ID NO 1
<211> LENGTH: 3192
<212> TYPE: DNA
<213> ORGANISM: Homo sapiens
<220> FEATURE:
<221> NAME/KEY: CDS
<222> LOCATION: (58)...(3006)

<400> SEQUENCE: 1

gaattcggct tcctggggga ttgtgtgact gttaaaataa ggtgaaaagc aataagg atg    60
                                                                Met
                                                                 1

ttt aag tgc tgg tca gtt gtc ttg gtt ctc gga ttc att ttt ctg gag      108
Phe Lys Cys Trp Ser Val Val Leu Val Leu Gly Phe Ile Phe Leu Glu
          5                  10                  15

tcg gaa gga agg cca acc aaa gaa gga gga tat ggc ctt aaa tcc tat      156
Ser Glu Gly Arg Pro Thr Lys Glu Gly Gly Tyr Gly Leu Lys Ser Tyr
         20                  25                  30

cag cct cta atg aga ttg cga cat aag cag gaa aaa aat caa gaa agt      204
Gln Pro Leu Met Arg Leu Arg His Lys Gln Glu Lys Asn Gln Glu Ser
     35                  40                  45

tca aga gtc aaa gga ttt atg att cag gat ggc cct ttt gga tct tgt      252
Ser Arg Val Lys Gly Phe Met Ile Gln Asp Gly Pro Phe Gly Ser Cys
 50                  55                  60                  65

gaa aat aag tac tgt ggt ttg gga aga cac tgt gtt acc agc aga gag      300
Glu Asn Lys Tyr Cys Gly Leu Gly Arg His Cys Val Thr Ser Arg Glu
                 70                  75                  80

aca ggg caa gca gaa tgt gcc tgt atg gac ctt tgc aaa cgt cac tac      348
Thr Gly Gln Ala Glu Cys Ala Cys Met Asp Leu Cys Lys Arg His Tyr
             85                  90                  95

aaa cct gtg tgt gga tct gac gga gaa ttc tat gaa aac cac tgt gaa      396
Lys Pro Val Cys Gly Ser Asp Gly Glu Phe Tyr Glu Asn His Cys Glu
        100                 105                 110

gtg cac aga gct gct tgc ctg aaa aaa caa aag att acc att gtt cac      444
Val His Arg Ala Ala Cys Leu Lys Lys Gln Lys Ile Thr Ile Val His
    115                 120                 125

aat gaa gac tgc ttc ttt aaa gga gat aag tgc aag act act gaa tac      492
Asn Glu Asp Cys Phe Phe Lys Gly Asp Lys Cys Lys Thr Thr Glu Tyr
130                 135                 140                 145

agc aag atg aaa aat atg cta tta gat tta caa aat caa aaa tat att      540
Ser Lys Met Lys Asn Met Leu Leu Asp Leu Gln Asn Gln Lys Tyr Ile
                150                 155                 160
```

-continued

```
atg caa gaa aat gaa aat cct aat ggc gac gac ata tct cgg aag aag      588
Met Gln Glu Asn Glu Asn Pro Asn Gly Asp Asp Ile Ser Arg Lys Lys
            165                 170                 175

cta ttg gtg gat caa atg ttt aaa tat ttt gat gca gac agt aat gga      636
Leu Leu Val Asp Gln Met Phe Lys Tyr Phe Asp Ala Asp Ser Asn Gly
        180                 185                 190

ctt gta gat att aat gaa cta act cag gtg ata aaa cag gaa gaa ctt      684
Leu Val Asp Ile Asn Glu Leu Thr Gln Val Ile Lys Gln Glu Glu Leu
    195                 200                 205

ggc aag gat ctc ttt gat tgt act ttg tat gtt cta ttg aaa tat gat      732
Gly Lys Asp Leu Phe Asp Cys Thr Leu Tyr Val Leu Leu Lys Tyr Asp
210                 215                 220                 225

gat ttt aat gct gac aag cac ctg gct ctt gaa gaa ttt tat aga gca      780
Asp Phe Asn Ala Asp Lys His Leu Ala Leu Glu Glu Phe Tyr Arg Ala
                230                 235                 240

ttc caa gtg atc cag ttg agt ctg cca gaa gat cag aaa cta agc atc      828
Phe Gln Val Ile Gln Leu Ser Leu Pro Glu Asp Gln Lys Leu Ser Ile
            245                 250                 255

act gca gca act gtg gga caa agt gct gtt ctg agc tgt gcc att caa      876
Thr Ala Ala Thr Val Gly Gln Ser Ala Val Leu Ser Cys Ala Ile Gln
        260                 265                 270

gga acc ctg aga cct ccc att atc tgg aaa agg aac aat att att cta      924
Gly Thr Leu Arg Pro Pro Ile Ile Trp Lys Arg Asn Asn Ile Ile Leu
    275                 280                 285

aat aat tta gat ttg gaa gac atc aat gac ttt gga gat gat ggg tcc      972
Asn Asn Leu Asp Leu Glu Asp Ile Asn Asp Phe Gly Asp Asp Gly Ser
290                 295                 300                 305

ttg tat att act aag gtt acc aca act cac gtt ggc aat tac acc tgc     1020
Leu Tyr Ile Thr Lys Val Thr Thr Thr His Val Gly Asn Tyr Thr Cys
                310                 315                 320

tat gca gat ggc tat gaa caa gtc tat cag act cac atc ttc caa gtg     1068
Tyr Ala Asp Gly Tyr Glu Gln Val Tyr Gln Thr His Ile Phe Gln Val
            325                 330                 335

aat gtt cct cca gtc atc cgg gtg tat cca gag agt cag gct aga gag     1116
Asn Val Pro Pro Val Ile Arg Val Tyr Pro Glu Ser Gln Ala Arg Glu
        340                 345                 350

cct ggg gta act gcc agt ctt agg tgc cat gca gag ggc ata cca aag     1164
Pro Gly Val Thr Ala Ser Leu Arg Cys His Ala Glu Gly Ile Pro Lys
    355                 360                 365

cct cag ctt ggc tgg ttg aag aat gga att gat att aca cca aag ctt     1212
Pro Gln Leu Gly Trp Leu Lys Asn Gly Ile Asp Ile Thr Pro Lys Leu
370                 375                 380                 385

tcc aaa caa ctc acg ctt caa gca aat ggc gca act gtg gga caa agt     1260
Ser Lys Gln Leu Thr Leu Gln Ala Asn Gly Ala Thr Val Gly Gln Ser
                390                 395                 400

gct gtt ctg agc tgt gcc att caa gga acc ctg aga cct ccc att atc     1308
Ala Val Leu Ser Cys Ala Ile Gln Gly Thr Leu Arg Pro Pro Ile Ile
            405                 410                 415

tgg aaa agg aac aat att att cta aat aat tta gat ttg gaa gac atc     1356
Trp Lys Arg Asn Asn Ile Ile Leu Asn Asn Leu Asp Leu Glu Asp Ile
        420                 425                 430

aat gac ttt gga gat gat ggg tcc ttg tat att act aag gtt acc aca     1404
Asn Asp Phe Gly Asp Asp Gly Ser Leu Tyr Ile Thr Lys Val Thr Thr
    435                 440                 445

act cac gtt ggc aat tac acc tgc tat gca gat ggc tat gaa caa gtc     1452
Thr His Val Gly Asn Tyr Thr Cys Tyr Ala Asp Gly Tyr Glu Gln Val
450                 455                 460                 465

tat cag act cac atc ttc caa gtg aat gtt cct cca gtc atc cgg gtg     1500
Tyr Gln Thr His Ile Phe Gln Val Asn Val Pro Pro Val Ile Arg Val
                470                 475                 480
```

-continued

```
tat cca gag agt cag gct aga gag cct ggg gta act gcc agt ctt agg     1548
Tyr Pro Glu Ser Gln Ala Arg Glu Pro Gly Val Thr Ala Ser Leu Arg
            485                 490                 495

tgc cat gca gag ggc ata cca aag cct cag ctt ggc tgg ttg aag aat     1596
Cys His Ala Glu Gly Ile Pro Lys Pro Gln Leu Gly Trp Leu Lys Asn
        500                 505                 510

gga att gat att aca cca aag ctt tcc aaa caa ctc acg ctt caa gca     1644
Gly Ile Asp Ile Thr Pro Lys Leu Ser Lys Gln Leu Thr Leu Gln Ala
    515                 520                 525

aat ggc agt gag gtt cac ata agc aat gtg cgc tat gaa gat act gga     1692
Asn Gly Ser Glu Val His Ile Ser Asn Val Arg Tyr Glu Asp Thr Gly
530                 535                 540                 545

gca tac act tgt atc gca aag aat gaa gca gga gtg gat gaa gac atc     1740
Ala Tyr Thr Cys Ile Ala Lys Asn Glu Ala Gly Val Asp Glu Asp Ile
                550                 555                 560

tct tct ctt ttt gtg gaa gac tct gct aga aag acc cta gct aac ata     1788
Ser Ser Leu Phe Val Glu Asp Ser Ala Arg Lys Thr Leu Ala Asn Ile
            565                 570                 575

tta tgg aga gaa gaa ggt ctg gga att ggg aac atg ttc tat gtt ttt     1836
Leu Trp Arg Glu Glu Gly Leu Gly Ile Gly Asn Met Phe Tyr Val Phe
        580                 585                 590

tat gaa gat gga atc aaa gtg ata caa ccc ata gaa tgt gaa ttt cag     1884
Tyr Glu Asp Gly Ile Lys Val Ile Gln Pro Ile Glu Cys Glu Phe Gln
    595                 600                 605

agg cac att aag cct agt gaa aag ctc ctt gga ttt cag gat gaa gtc     1932
Arg His Ile Lys Pro Ser Glu Lys Leu Leu Gly Phe Gln Asp Glu Val
610                 615                 620                 625

tgt ccc aaa gct gag gga gat gaa gtt cag agg tgt gtg tgg gca tca     1980
Cys Pro Lys Ala Glu Gly Asp Glu Val Gln Arg Cys Val Trp Ala Ser
                630                 635                 640

gct gtt aat gtc aaa gac aag ttc att tat gtt gca cag cca act ttg     2028
Ala Val Asn Val Lys Asp Lys Phe Ile Tyr Val Ala Gln Pro Thr Leu
            645                 650                 655

gac aga gtc ctt att gtt gat gtg cag tcc caa aaa gtt gtt cag gca     2076
Asp Arg Val Leu Ile Val Asp Val Gln Ser Gln Lys Val Val Gln Ala
        660                 665                 670

gtg agc aca gac cct gtc cca gtt aaa tta cac tat gac aaa tca cat     2124
Val Ser Thr Asp Pro Val Pro Val Lys Leu His Tyr Asp Lys Ser His
    675                 680                 685

gat cag gtc tgg gtg cta agc tgg ggt acc ttg gag aag aca tca cca     2172
Asp Gln Val Trp Val Leu Ser Trp Gly Thr Leu Glu Lys Thr Ser Pro
690                 695                 700                 705

aca cta cag gta att acc ctg gcc agt ggg aat gtg cct cac cac acg     2220
Thr Leu Gln Val Ile Thr Leu Ala Ser Gly Asn Val Pro His His Thr
                710                 715                 720

atc cac acc caa cca gtg gga aag caa ttt gac aga gtg gat gat ttt     2268
Ile His Thr Gln Pro Val Gly Lys Gln Phe Asp Arg Val Asp Asp Phe
            725                 730                 735

ttc att ccc acc aca aca ctc att atc acc cat atg agg ttt gga ttt     2316
Phe Ile Pro Thr Thr Thr Leu Ile Ile Thr His Met Arg Phe Gly Phe
        740                 745                 750

att ctt cat aaa gat gaa gct gca cta caa aaa att gat ctt gaa acc     2364
Ile Leu His Lys Asp Glu Ala Ala Leu Gln Lys Ile Asp Leu Glu Thr
    755                 760                 765

atg tca tac atc aag aca att aac ttg aag gac tat aag tgc gtt cct     2412
Met Ser Tyr Ile Lys Thr Ile Asn Leu Lys Asp Tyr Lys Cys Val Pro
770                 775                 780                 785

cag tca ttg gca tat aca cac ttg gga ggc tac tac ttc att ggc tgc     2460
Gln Ser Leu Ala Tyr Thr His Leu Gly Gly Tyr Tyr Phe Ile Gly Cys
```

-continued

```
            790                 795                 800

aaa cct gac agc acc gga gca gtt tcc cca cag gtc atg gtg gac ggt     2508
Lys Pro Asp Ser Thr Gly Ala Val Ser Pro Gln Val Met Val Asp Gly
            805                 810                 815

gta act gac tca gtc att ggg ttc aat agt gat gtg acg ggc act cca     2556
Val Thr Asp Ser Val Ile Gly Phe Asn Ser Asp Val Thr Gly Thr Pro
        820                 825                 830

tat gtc tct cca gat ggc cac tac ctt gtc agc att aat gat gtg aaa     2604
Tyr Val Ser Pro Asp Gly His Tyr Leu Val Ser Ile Asn Asp Val Lys
    835                 840                 845

ggt ctt gta agg gtt cag tac att acc atc aga gga gaa ata cag gag     2652
Gly Leu Val Arg Val Gln Tyr Ile Thr Ile Arg Gly Glu Ile Gln Glu
850                 855                 860                 865

gct ttt gat att tac aca aat ctg cac ata tct gat ctg gca ttt caa     2700
Ala Phe Asp Ile Tyr Thr Asn Leu His Ile Ser Asp Leu Ala Phe Gln
                870                 875                 880

cca tcc ttt act gaa gcc cac caa tat aac atc tac ggt agt tca agc     2748
Pro Ser Phe Thr Glu Ala His Gln Tyr Asn Ile Tyr Gly Ser Ser Ser
            885                 890                 895

aca caa act gat gtg ctc ttt gtg gag ctc tct tct ggg aag gtc aag     2796
Thr Gln Thr Asp Val Leu Phe Val Glu Leu Ser Ser Gly Lys Val Lys
        900                 905                 910

atg ata aag agt ctc aag gaa cca ctc aag gca gaa gaa tgg cct tgg     2844
Met Ile Lys Ser Leu Lys Glu Pro Leu Lys Ala Glu Glu Trp Pro Trp
    915                 920                 925

aac cgg aaa aac agg caa atc cag gac agt ggc ttg ttt ggt caa tac     2892
Asn Arg Lys Asn Arg Gln Ile Gln Asp Ser Gly Leu Phe Gly Gln Tyr
930                 935                 940                 945

ctg atg aca cct tcc aag gac tct ctc ttc atc cta gat gga cga ctc     2940
Leu Met Thr Pro Ser Lys Asp Ser Leu Phe Ile Leu Asp Gly Arg Leu
                950                 955                 960

aat aaa tta aac tgt gag atc act gaa gtt gaa aaa gga aat aca gtc     2988
Asn Lys Leu Asn Cys Glu Ile Thr Glu Val Glu Lys Gly Asn Thr Val
            965                 970                 975

att tgg gtt gga gat gcc taaaaaccct acgatacaat tattgaatga            3036
Ile Trp Val Gly Asp Ala
        980

agcgttttac aatacattgc acttaatcca ttgtttaaat ttacaactta actttccaag   3096

tttatatcct agtcaaacaa aatttacttg gttggtccaa ataaaataaa ttgtttttga   3156

ctaagaaaaa aaaaaaaaaa aaattcctgc ggccgc                             3192


<210> SEQ ID NO 2
<211> LENGTH: 983
<212> TYPE: PRT
<213> ORGANISM: Homo sapiens

<400> SEQUENCE: 2

Met Phe Lys Cys Trp Ser Val Val Leu Val Leu Gly Phe Ile Phe Leu
 1               5                  10                  15

Glu Ser Glu Gly Arg Pro Thr Lys Glu Gly Gly Tyr Gly Leu Lys Ser
            20                  25                  30

Tyr Gln Pro Leu Met Arg Leu Arg His Lys Gln Glu Lys Asn Gln Glu
        35                  40                  45

Ser Ser Arg Val Lys Gly Phe Met Ile Gln Asp Gly Pro Phe Gly Ser
    50                  55                  60

Cys Glu Asn Lys Tyr Cys Gly Leu Gly Arg His Cys Val Thr Ser Arg
65                  70                  75                  80
```

-continued

```
Glu Thr Gly Gln Ala Glu Cys Ala Cys Met Asp Leu Cys Lys Arg His
                85                  90                  95

Tyr Lys Pro Val Cys Gly Ser Asp Gly Glu Phe Tyr Glu Asn His Cys
            100                 105                 110

Glu Val His Arg Ala Ala Cys Leu Lys Lys Gln Lys Ile Thr Ile Val
        115                 120                 125

His Asn Glu Asp Cys Phe Phe Lys Gly Asp Lys Cys Lys Thr Thr Glu
    130                 135                 140

Tyr Ser Lys Met Lys Asn Met Leu Leu Asp Leu Gln Asn Gln Lys Tyr
145                 150                 155                 160

Ile Met Gln Glu Asn Glu Asn Pro Asn Gly Asp Asp Ile Ser Arg Lys
                165                 170                 175

Lys Leu Leu Val Asp Gln Met Phe Lys Tyr Phe Asp Ala Asp Ser Asn
            180                 185                 190

Gly Leu Val Asp Ile Asn Glu Leu Thr Gln Val Ile Lys Gln Glu Glu
        195                 200                 205

Leu Gly Lys Asp Leu Phe Asp Cys Thr Leu Tyr Val Leu Leu Lys Tyr
    210                 215                 220

Asp Asp Phe Asn Ala Asp Lys His Leu Ala Leu Glu Glu Phe Tyr Arg
225                 230                 235                 240

Ala Phe Gln Val Ile Gln Leu Ser Leu Pro Glu Asp Gln Lys Leu Ser
                245                 250                 255

Ile Thr Ala Ala Thr Val Gly Gln Ser Ala Val Leu Ser Cys Ala Ile
            260                 265                 270

Gln Gly Thr Leu Arg Pro Pro Ile Ile Trp Lys Arg Asn Asn Ile Ile
        275                 280                 285

Leu Asn Asn Leu Asp Leu Glu Asp Ile Asn Asp Phe Gly Asp Asp Gly
    290                 295                 300

Ser Leu Tyr Ile Thr Lys Val Thr Thr Thr His Val Gly Asn Tyr Thr
305                 310                 315                 320

Cys Tyr Ala Asp Gly Tyr Glu Gln Val Tyr Gln Thr His Ile Phe Gln
                325                 330                 335

Val Asn Val Pro Pro Val Ile Arg Val Tyr Pro Glu Ser Gln Ala Arg
            340                 345                 350

Glu Pro Gly Val Thr Ala Ser Leu Arg Cys His Ala Glu Gly Ile Pro
        355                 360                 365

Lys Pro Gln Leu Gly Trp Leu Lys Asn Gly Ile Asp Ile Thr Pro Lys
    370                 375                 380

Leu Ser Lys Gln Leu Thr Leu Gln Ala Asn Gly Ala Thr Val Gly Gln
385                 390                 395                 400

Ser Ala Val Leu Ser Cys Ala Ile Gln Gly Thr Leu Arg Pro Pro Ile
                405                 410                 415

Ile Trp Lys Arg Asn Asn Ile Ile Leu Asn Asn Leu Asp Leu Glu Asp
            420                 425                 430

Ile Asn Asp Phe Gly Asp Asp Gly Ser Leu Tyr Ile Thr Lys Val Thr
        435                 440                 445

Thr Thr His Val Gly Asn Tyr Thr Cys Tyr Ala Asp Gly Tyr Glu Gln
    450                 455                 460

Val Tyr Gln Thr His Ile Phe Gln Val Asn Val Pro Pro Val Ile Arg
465                 470                 475                 480

Val Tyr Pro Glu Ser Gln Ala Arg Glu Pro Gly Val Thr Ala Ser Leu
                485                 490                 495

Arg Cys His Ala Glu Gly Ile Pro Lys Pro Gln Leu Gly Trp Leu Lys
```

-continued

```
            500                 505                 510

Asn Gly Ile Asp Ile Thr Pro Lys Leu Ser Lys Gln Leu Thr Leu Gln
        515                 520                 525

Ala Asn Gly Ser Glu Val His Ile Ser Asn Val Arg Tyr Glu Asp Thr
    530                 535                 540

Gly Ala Tyr Thr Cys Ile Ala Lys Asn Glu Ala Gly Val Asp Glu Asp
545                 550                 555                 560

Ile Ser Ser Leu Phe Val Glu Asp Ser Ala Arg Lys Thr Leu Ala Asn
                565                 570                 575

Ile Leu Trp Arg Glu Glu Gly Leu Gly Ile Gly Asn Met Phe Tyr Val
            580                 585                 590

Phe Tyr Glu Asp Gly Ile Lys Val Ile Gln Pro Ile Glu Cys Glu Phe
        595                 600                 605

Gln Arg His Ile Lys Pro Ser Glu Lys Leu Leu Gly Phe Gln Asp Glu
    610                 615                 620

Val Cys Pro Lys Ala Glu Gly Asp Glu Val Gln Arg Cys Val Trp Ala
625                 630                 635                 640

Ser Ala Val Asn Val Lys Asp Lys Phe Ile Tyr Val Ala Gln Pro Thr
                645                 650                 655

Leu Asp Arg Val Leu Ile Val Asp Val Gln Ser Gln Lys Val Val Gln
            660                 665                 670

Ala Val Ser Thr Asp Pro Val Pro Val Lys Leu His Tyr Asp Lys Ser
        675                 680                 685

His Asp Gln Val Trp Val Leu Ser Trp Gly Thr Leu Glu Lys Thr Ser
    690                 695                 700

Pro Thr Leu Gln Val Ile Thr Leu Ala Ser Gly Asn Val Pro His His
705                 710                 715                 720

Thr Ile His Thr Gln Pro Val Gly Lys Gln Phe Asp Arg Val Asp Asp
                725                 730                 735

Phe Phe Ile Pro Thr Thr Thr Leu Ile Ile Thr His Met Arg Phe Gly
            740                 745                 750

Phe Ile Leu His Lys Asp Glu Ala Ala Leu Gln Lys Ile Asp Leu Glu
        755                 760                 765

Thr Met Ser Tyr Ile Lys Thr Ile Asn Leu Lys Asp Tyr Lys Cys Val
    770                 775                 780

Pro Gln Ser Leu Ala Tyr Thr His Leu Gly Gly Tyr Tyr Phe Ile Gly
785                 790                 795                 800

Cys Lys Pro Asp Ser Thr Gly Ala Val Ser Pro Gln Val Met Val Asp
                805                 810                 815

Gly Val Thr Asp Ser Val Ile Gly Phe Asn Ser Asp Val Thr Gly Thr
            820                 825                 830

Pro Tyr Val Ser Pro Asp Gly His Tyr Leu Val Ser Ile Asn Asp Val
        835                 840                 845

Lys Gly Leu Val Arg Val Gln Tyr Ile Thr Ile Arg Gly Glu Ile Gln
    850                 855                 860

Glu Ala Phe Asp Ile Tyr Thr Asn Leu His Ile Ser Asp Leu Ala Phe
865                 870                 875                 880

Gln Pro Ser Phe Thr Glu Ala His Gln Tyr Asn Ile Tyr Gly Ser Ser
                885                 890                 895

Ser Thr Gln Thr Asp Val Leu Phe Val Glu Leu Ser Ser Gly Lys Val
            900                 905                 910

Lys Met Ile Lys Ser Leu Lys Glu Pro Leu Lys Ala Glu Glu Trp Pro
        915                 920                 925
```

-continued

```
Trp Asn Arg Lys Asn Arg Gln Ile Gln Asp Ser Gly Leu Phe Gly Gln
    930                 935                 940

Tyr Leu Met Thr Pro Ser Lys Asp Ser Leu Phe Ile Leu Asp Gly Arg
945                 950                 955                 960

Leu Asn Lys Leu Asn Cys Glu Ile Thr Glu Val Glu Lys Gly Asn Thr
                965                 970                 975

Val Ile Trp Val Gly Asp Ala
            980


<210> SEQ ID NO 3
<211> LENGTH: 2949
<212> TYPE: DNA
<213> ORGANISM: Artificial Sequence
<220> FEATURE:
<223> OTHER INFORMATION: Degenerate oligonucleotide sequence encoding
      the zfsta2 polypeptide of SEQ ID NO:2.
<221> NAME/KEY: variation
<222> LOCATION: (1)...(2949)
<223> OTHER INFORMATION: Each N is independently any nucleotide.

<400> SEQUENCE: 3

atgttyaart gytggwsngt ngtnytngtn ytnggnttya thttyytnga rwsngarggn     60

mgnccnacna argarggngg ntayggnytn aarwsntayc arccnytnat gmgnytnmgn    120

cayaarcarg araaraayca rgarwsnwsn mgngtnaarg gnttyatgat hcargayggn    180

ccnttyggnw sntgygaraa yaartaytgy ggnytnggnm gncaytgygt nacnwsnmgn    240

garacnggnc argcngartg ygcntgyatg gayytntgya armgncayta yaarccngtn    300

tgyggnwsng ayggngartt ytaygaraay caytgygarg tncaymgngc ngcntgyytn    360

aaraarcara arathacnat hgtncayaay gargaytgyt tyttyaargg ngayaartgy    420

aaracnacng artaywsnaa ratgaaraay atgytnytng ayytncaraa ycaraartay    480

athatgcarg araaygaraa yccnaayggn gaygayathw snmgnaaraa rytnytngtn    540

gaycaratgt tyaartaytt ygaygcngay wsnaayggny tngtngayat haaygarytn    600

acncargtna thaarcarga rgarytnggn aargayytnt tygaytgyac nytntaygtn    660

ytnytnaart aygaygaytt yaaygcngay aarcayytng cnytngarga rttytaymgn    720

gcnttycarg tnathcaryt nwsnytnccn gargaycara arytnwsnat hacngcngcn    780

acngtnggnc arwsngcngt nytnwsntgy gcnathcarg gnacnytnmg nccnccnath    840

athtggaarm gnaayaayat hathytnaay aayytngayy tngargayat haaygaytty    900

ggngaygayg gnwsnytnta yathacnaar gtnacnacna cncaygtngg naaytayacn    960

tgytaygcng ayggntayga rcargtntay caracncaya thttycargt naaygtnccn   1020

ccngtnathm gngtntaycc ngarwsncar gcnmgngarc cnggngtnac ngcnwsnytn   1080

mgntgycayg cngarggnat hccnaarccn carytnggnt ggytnaaraa yggnathgay   1140

athacnccna arytnwsnaa rcarytnacn ytncargcna ayggngcnac ngtnggncar   1200

wsngcngtny tnwsntgygc nathcarggn acnytnmgnc cnccnathat htggaarmgn   1260

aayaayatha thytnaayaa yytngayytn gargayatha aygayttygg ngaygayggn   1320

wsnytntaya thacnaargt nacnacnacn caygtnggna aytayacntg ytaygcngay   1380

ggntaygarc argtntayca racncayath ttycargtna aygtnccncc ngtnathmgn   1440

gtntayccng arwsncargc nmgngarccn ggngtnacng cnwsnytnmg ntgycaygcn   1500

garggnathc cnaarccnca rytnggntgg ytnaaraayg gnathgayat hacnccnaar   1560
```

-continued

```
ytnwsnaarc arytnacnyt ncargcnaay ggnwsngarg tncayathws naaygtnmgn   1620

taygargaya cnggngcnta yacntgyath gcnaaraayg argcnggngt ngaygargay   1680

athwsnwsny tnttygtnga rgaywsngcn mgnaaracny tngcnaayat hytntggmgn   1740

gargarggny tnggnathgg naayatgtty taygtnttyt aygargaygg nathaargtn   1800

athcarccna thgartgyga rttycarmgn cayathaarc cnwsngaraa rytnytnggn   1860

ttycargayg argtntgycc naargcngar ggngaygarg tncarmgntg ygtntgggcn   1920

wsngcngtna aygtnaarga yaarttyath taygtngcnc arccnacnyt ngaymgngtn   1980

ytnathgtng aygtncarws ncaraargtn gtncargcng tnwsnacnga yccngtnccn   2040

gtnaarytnc aytaygayaa rwsncaygay cargtntggg tnytnwsntg gggnacnytn   2100

garaaracnw sccnacnyt ncargtnath acnytngcnw snggnaaygt nccncaycay   2160

acnathcaya cncarccngt nggnaarcar ttygaymgng tngaygaytt yttyathccn   2220

acnacnacny tnathathac ncayatgmgn ttyggnttya thytncayaa rgaygargcn   2280

gcnytncara arathgayyt ngaracnatg wsntayatha aracnathaa yytnaargay   2340

tayaartgyg tnccncarws nytngcntay acncayytng gnggntayta yttyathggn   2400

tgyaarccng aywsnacngg ngcngtnwsn ccncargtna tggtngaygg ngtnacngay   2460

wsngtnathg gnttyaayws ngaygtnacn ggnacnccnt aygtnwsncc ngayggncay   2520

tayytngtnw snathaayga ygtnaarggn ytngtnmgng tncartayat hacnathmgn   2580

ggngarathc argargcntt ygayathtay acnaayytnc ayathwsnga yytngcntty   2640

carccnwsnt tyacngargc ncaycartay aayathtayg gnwsnwsnws nacncaracn   2700

gaygtnytnt tygtngaryt nwsnwsnggn aargtnaara tgathaarws nytnaargar   2760

ccnytnaarg cngargartg gccntggaay mgnaaraaym gncarathca rgaywsnggn   2820

ytnttyggnc artayytnat gacnccnwsn aargaywsny tnttyathyt ngayggnmgn   2880

ytnaayaary tnaaytgyga rathacngar gtngaraarg gnaayacngt nathtgggtn   2940

ggngaygcn                                                           2949
```

```
<210> SEQ ID NO 4
<211> LENGTH: 147
<212> TYPE: DNA
<213> ORGANISM: Artificial Sequence
<220> FEATURE:
<223> OTHER INFORMATION: 147 bp probe

<400> SEQUENCE: 4

ggatttatga ttcaggatgg cccttttgga tcttgtgaaa ataagtactg tggtttngga     60

agacactgtg ttacccagca gagagacagg gcaagcagaa tgtgcctgta tggacctttg    120

caaacgtcac tacaaacctg tgtgtgg                                        147


<210> SEQ ID NO 5
<211> LENGTH: 25
<212> TYPE: DNA
<213> ORGANISM: Artificial Sequence
<220> FEATURE:
<223> OTHER INFORMATION: Oligonucleotide ZC18415

<400> SEQUENCE: 5

cctgggggat tgtgtgactg ttaaa                                           25


<210> SEQ ID NO 6
<211> LENGTH: 24
```

-continued

<212> TYPE: DNA
<213> ORGANISM: Artificial Sequence
<220> FEATURE:
<223> OTHER INFORMATION: Oligonucleotide ZC14701

<400> SEQUENCE: 6
ctgccatttg cttgaagcgt gagt 24

<210> SEQ ID NO 7
<211> LENGTH: 1255
<212> TYPE: DNA
<213> ORGANISM: Artificial Sequence
<220> FEATURE:
<223> OTHER INFORMATION: 3' end of zfsta2 nucleotide sequence

<400> SEQUENCE: 7
gaattcggct tcctggggga ttgtgtgact gttaaaataa ggtgaaaagc aataaggatg 60
tttaagtgct ggtcagttgt cttggttctc ggattcattt ttctggagtc ggaaggaagg 120
ccaaccaaag aaggaggata tggccttaaa tcctatcagc ctctaatgag attgcgacat 180
aagcaggaaa aaaatcaaga aagttcaaga gtcaaaggat ttatgattca ggatggccct 240
tttggatctt gtgaaaataa gtactgtggt ttgggaagac actgtgttac cagcagagag 300
acagggcaag cagaatgtgc ctgtatggac ctttgcaaac gtcactacaa acctgtgtgt 360
ggatctgacg gagaattcta tgaaaaccac tgtgaagtgc acagagctgc ttgcctgaaa 420
aaacaaaaga ttaccattgt tcacaatgaa gactgcttct ttaaaggaga taagtgcaag 480
actactgaat acagcaagat gaaaaatatg ctattagatt tacaaaatca aaaatatatt 540
atgcaagaaa atgaaaatcc taatggcgac gacatatctc ggaagaagct attggtggat 600
caaatgttta aatattttga tgcagacagt aatggacttg tagatattaa tgaactaact 660
caggtgataa aacaggaaga acttggcaag gatctctttg attgtacttt gtatgttcta 720
ttgaaatatg atgattttaa tgctgacaag cacctggctc ttgaagaatt ttatagagca 780
ttccaagtga tccagttgag tctgccagaa gatcagaaac taagcatcac tgcagcaact 840
gtgggacaaa gtgctgttct gagctgtgcc attcaaggaa ccctgagacc tcccattatc 900
tggaaaagga acaatattat tctaaataat ttagatttgg aagacatcaa tgactttgga 960
gatgatgggt ccttgtatat tactaaggtt accacaactc acgttggcaa ttacacctgc 1020
tatgcagatg gctatgaaca agtctatcag actcacatct tccaagtgaa tgttcctcca 1080
gtcatccggg tgtatccaga gagtcaggct agagagcctg ggtaactgc cagtcttagg 1140 tgccatgcag agggcatacc aaagcctcag cttggctggt tgaagaatgg aattgatatt 1200
acaccaaagc tttccaaaca actcacgctt caagcaaatg gcagaagccg aattc 1255

<210> SEQ ID NO 8
<211> LENGTH: 1896
<212> TYPE: DNA
<213> ORGANISM: Artificial Sequence
<220> FEATURE:
<223> OTHER INFORMATION: 5' end of zfsta2 nucleotide sequence

<400> SEQUENCE: 8
aagcttggca cgagggcaac tgtgggacaa agtgctgttc tgagctgtgc cattcaagga 60
accctgagac ctcccattat ctggaaaagg aacaatatta ttctaaataa tttagatttg 120
gaagacatca atgactttgg agatgatggg tccttgtata ttactaaggt taccacaact 180
cacgttggca attacacctg ctatgcagat ggctatgaac aagtctatca gactcacatc 240

-continued

```
ttccaagtga atgttcctcc agtcatccgg gtgtatccag agagtcaggc tagagagcct    300

ggggtaactg ccagtcttag gtgccatgca gagggcatac caaagcctca gcttggctgg    360

ttgaagaatg gaattgatat tacaccaaag ctttccaaac aactcacgct tcaagcaaat    420

ggcagtgagg ttcacataag caatgtgcgc tatgaagata ctggagcata cacttgtatc    480

gcaaagaatg aagcaggagt ggatgaagac atctcttctc tttttgtgga agactctgct    540

agaaagaccc tagctaacat attatggaga gaagaaggtc tgggaattgg gaacatgttc    600

tatgtttttt atgaagatgg aatcaaagtg atacaaccca tagaatgtga atttcagagg    660

cacattaagc ctagtgaaaa gctccttgga tttcaggatg aagtctgtcc caaagctgag    720

ggagatgaag ttcagaggtg tgtgtgggca tcagctgtta atgtcaaaga caagttcatt    780

tatgttgcac agccaacttt ggacagagtc cttattgttg atgtgcagga tcaggtctgg    840

gtgctaagct ggggtacctt ggagaagaca tcaccaacac tacaggtaat taccctggcc    900

agtgggaatg tgcctcacca cacgatccac acccaaccag tgggaaagca atttgacaga    960

gtggatgatt ttttcattcc caccacaaca ctcattatca cccatatgag gtttggattt   1020

attcttcata aagatgaagc tgcactacaa aaaattgatc ttgaaaccat gtcatacatc   1080

aagacaatta acttgaagga ctataagtgc gttcctcagt cattggcata tacacacttg   1140

ggaggctact acttcattgg ctgcaaacct gacagcaccg gagcagtttc cccacaggtc   1200

atggtggacg gtgtaactga ctcagtcatt gggttcaata gtgatgtgac gggcactcca   1260

tatgtctctc cagatggcca ctaccttgtc agcattaatg atgtgaaagg tcttgtaagg   1320

gttcagtaca ttaccatcag aggagaaata caggaggctt ttgatattta cacaaatctg   1380

cacatatctg atctggcatt tcaaccatcc tttactgaag cccaccaata taacatctac   1440

ggtagttcaa gcacacaaac tgatgtgctc tttgtggagc tctcttctgg gaaggtcaag   1500

atgataaaga gtctcaagga accactcaag gcagaagaat ggccttggaa ccggaaaaac   1560

aggcaaatcc aggacagtgg cttgtttggt caatacctga tgacaccttc caaggactct   1620

ctcttcatcc tagatggacg actcaataaa ttaaactgtg agatcactga agttgaaaaa   1680

ggaaatacag tcatttgggt tggagatgcc taaaaaccct acgatacaat tattgaatga   1740

agcgttttac aatacattgc acttaatcca ttgtttaaat ttacaactta actttccaag   1800

tttatatcct agtcaaacaa aatttacttg gttggtccaa ataaaataaa ttgtttttga   1860

ctaagaaaaa aaaaaaaaaa aaattcctgc ggccgc                             1896


<210> SEQ ID NO 9
<211> LENGTH: 23
<212> TYPE: DNA
<213> ORGANISM: Artificial Sequence
<220> FEATURE:
<223> OTHER INFORMATION: Oligonucleotide ZC12881

<400> SEQUENCE: 9

ggatttatga ttcaggatgg ccc                                             23


<210> SEQ ID NO 10
<211> LENGTH: 22
<212> TYPE: DNA
<213> ORGANISM: Artificial Sequence
<220> FEATURE:
<223> OTHER INFORMATION: Oligonucleotide ZC12884

<400> SEQUENCE: 10

ccacacacag gtttgtagtg ac                                              22
```

-continued

```
<210> SEQ ID NO 11
<211> LENGTH: 18
<212> TYPE: DNA
<213> ORGANISM: Artificial Sequence
<220> FEATURE:
<223> OTHER INFORMATION: Oligonucleotide ZC15510

<400> SEQUENCE: 11

tggacggtgt aactgact                                                    18


<210> SEQ ID NO 12
<211> LENGTH: 18
<212> TYPE: DNA
<213> ORGANISM: Artificial Sequence
<220> FEATURE:
<223> OTHER INFORMATION: Oligonucleotide ZC15575

<400> SEQUENCE: 12

aagcctcctg tatttctc                                                    18


<210> SEQ ID NO 13
<211> LENGTH: 12
<212> TYPE: DNA
<213> ORGANISM: Artificial Sequence
<220> FEATURE:
<223> OTHER INFORMATION: Contig example

<400> SEQUENCE: 13

atggcttagc tt                                                          12


<210> SEQ ID NO 14
<211> LENGTH: 12
<212> TYPE: DNA
<213> ORGANISM: Artificial Sequence
<220> FEATURE:
<223> OTHER INFORMATION: Contig example

<400> SEQUENCE: 14

tagcttgagt ct                                                          12


<210> SEQ ID NO 15
<211> LENGTH: 12
<212> TYPE: DNA
<213> ORGANISM: Artificial Sequence
<220> FEATURE:
<223> OTHER INFORMATION: Contig example

<400> SEQUENCE: 15

gtcgactacc ga                                                          12
```

FOLLISTATIN-RELATED PROTEIN ZFSTA2

REFERENCE TO RELATED APPLICATIONS

This application is related to Provisional Application No. 60/104,431, filed on Oct. 15, 1998. Under 35 U.S.C. §119(e) (1), this application claims benefit of said Provisional Application.

BACKGROUND OF THE INVENTION

Follistatin is a monomeric, glycosylated protein originally identified in porcine follicular fluid as a potent inhibitor of pituitary follicle-stimulating hormone (FSH) synthesis and secretion, follistatin was later shown to exert some of its biological effects by specifically binding the FSH-inducer activin. Other follistatin family members include follistatin related protein or FRP (Zwijsen et al., *Eur. J. Biochem.* 225:937–46, 1994), SPARC, also known as osteonectin or BM-40 or the human ortholog of mouse TSC-36 (Lane and Sage, ibid.), agrin (Patthy and Nikolics, *TINS* 16:76–81, 1993), hevin (Girard and Springer, *Immunity* 2:113–23, 1995), the Flik protein of chickens (Amthor et al., *Dev. Biology* 178:343–62, 1996) and the rat brain protein SC1 (Mendis et al., *Brain Res.* 730:95–106, 1996). Follistatins, however, are thought to be more than "activin binders" since follistatin deficient mice prepared by gene targeting have a more complex and different phenotype than activin gene knock-out animals (Mazuk et al., *Nature* 374:360–3, 1995 and Mazuk et al., *Nature* 374:356–9, 1995).

Activins and inhibins are potent activators and inhibitors, respectively, of pituitary FSH secretion and are members of the TGF-β family of peptide growth factors (Mather et al.,*Proc. Soc. Exp. Biol. Med.* 215:209–22, 1997). The activin and inhibin family of hormones, while originally described as gonadally produced regulators of pituitary FSH secretion, are now known to have a broad range of effects within and outside of the reproductive system (Mather et al., ibid.). Inhibins consist of a common alpha subunit which is covalently linked to one of two different beta subunits (inhibin A:$\alpha/B_A$; inhibin B:$\alpha/B_B$); activins are covalently linked dimers of the two B-subunits and therefore exist in three different forms (activin A:$B_A/B_A$; activin B:$B_B/B_B$; activin AB:$B_A/B_B$). Activin and inhibin bind to follistatin with high affinity, and although the structure of the activin binding site has not been completely defined, preliminary data (Inouye et al., *Biochem. Biophys. Res. Commun.* 179:352–8, 1991) suggest that residues in the first amino terminal cysteine-rich follistatin domain are involved in hormone binding. Activin binding to follistatin is thus thought to limit its biological effects by sequestration of the peptide hormone. Thus, the broad range of biological actions of the activins and inhibins, and possibly other members of the TGF-β family as well, may be regulated by binding to proteins of the follistatin family. Different binding proteins may be involved for each TGF-β family member as follistatin binds activin with high affinity (nM), inhibin with lower affinity, and does not appear to bind TGF-β at all (Mather et al., ibid.). Follistatin family members may regulate the activity of other growth factors as well, for example, SPARC or BM-40 have been shown to bind platelet derived growth factor (PDGF-AB, PDGF-BB) (Lane and Sage, *FASEB J.* 8:163–73, 1994).

This application provides a new member of the follistatin family, zfsta2, which is likely to play a major role in regulating the biological activities of the TGF-β growth factors. Like other members of the follistatin family, zfsta2 may play a broad role in development and differentiation, pathogenesis of atherosclerosis, regulation of the gonadal-pituitary-hypothalamic axis, tooth and bone formation, regulation of gonadal hormone production, spermatogenesis, hypothalmic oxytocin secretion, proliferation and differentiation of erythroid progenitors, hematopoiesis, host defense and neuron survival.

The present invention provides such polypeptides for these and other uses that should be apparent to those skilled in the art from the teachings herein.

SUMMARY OF THE INVENTION

Within one aspect the invention provides an isolated polypeptide comprising a follistatin homology domain, wherein the follistatin homology domain comprises amino acid residues 65 to 133 of the amino acid sequence of SEQ ID NO:2. Within one embodiment the polypeptide further comprises an alpha helical linker region that resides in a carboxyl-terminal position relative to the follistatin homology domain, wherein the alpha helical linker region comprises amino acid residues 134 to 174 of the amino acid sequence of SEQ ID NO:2. Within a related embodiment the polypeptide further comprises a calmodulin homology domain that resides in a carboxyl-terminal position relative to the alpha helical linker region, wherein the calmodulin homology domain comprises amino acid residues 175 to 250 of the amino acid sequence of SEQ ID NO:2. Within another embodiment the polypeptide further comprises two I-set Ig domains that reside in a carboxyl-terminal position relative to the calmodulin homology domain, wherein the I-set Ig domains comprise amino acid residues 251 to 431 of the amino acid sequence of SEQ ID NO:2. Within another embodiment the polypeptide further comprises a carboxy-terminal domain that resides in a carboxyl-terminal position relative to the I-set Ig domains, wherein the carboxy-terminal domain comprises amino acid residues 433 to 847 of the amino acid sequence of SEQ ID NO:2. Within a yet another embodiment the polypeptide further comprises a hydrophilic linker region that resides in an amino-terminal position relative to the follistatin homology domain, wherein the hydrophobic linker region comprises amino acid residues 21 to 64 of the amino acid sequence of SEQ ID NO:2. Within another embodiment the polypeptide further comprises a secretory signal sequence that resides in an amino-terminal position relative to the hydrophobic linker region, wherein the secretory signal sequence comprises amino acid residues 1 to 20 of the amino acid sequence of SEQ ID NO:2.

Within another aspect the invention provides an isolated polypeptide having an amino acid sequence that is at least 70% identical to the amino acid sequence of SEQ ID NO:2, wherein the isolated polypeptide specifically binds with an antibody to which a polypeptide having the amino acid sequence of SEQ ID NO:2 specifically binds. Within one embodiment the isolated polypeptide has an amino acid sequence that is at least 80% identical to the amino acid sequence of SEQ ID NO:2. Within another embodiment the isolated polypeptide has an amino acid sequence that is at least 90% identical to the amino acid sequence of SEQ ID NO:2. Within a further embodiment any difference between the amino acid sequence and the corresponding amino acid sequence of SEQ ID NO:2 is due to one or more conservative amino acid substitutions. Within another embodiment the amino acid percent identity is determined using a FASTA program with ktup=1, gap opening penalty=10, gap extension penalty=1, and substitution matrix=blosum62, with other parameters set as default.

The invention also provides an isolated polypeptide comprising the amino acid sequence of SEQ ID NO:2.

The invention further provides an isolated polypeptide selected from the group consisting of: a) a polypeptide consisting of the sequence of amino acid residues from residue 21 to residue 64 of SEQ ID NO:2; b) a polypeptide consisting of the sequence of amino acid residues from residue 65 to residue 133 of SEQ ID NO:2; c) a polypeptide consisting of the sequence of amino acid residues from residue 134 to residue 174 of SEQ ID NO:2; d) a polypeptide consisting of the sequence of amino acid residues from residue 175 to residue 250 of SEQ ID NO:2; e) a polypeptide consisting of the sequence of amino acid residues from residue 251 to residue 334 of SEQ ID NO:2; f) a polypeptide consisting of the sequence of amino acid residues from residue 335 to residue 432 of SEQ ID NO:2; g) a polypeptide consisting of the sequence of amino acid residues from residue 433 to residue 847 of SEQ ID NO:2; h) a polypeptide consisting of the sequence of amino acid residues from residue 251 to residue 432 of SEQ ID NO:2; i) a polypeptide consisting of the sequence of amino acid residues from residue 65 to residue 174 of SEQ ID NO:2; j) a polypeptide consisting of the sequence of amino acid residues from residue 65 to residue 250 of SEQ ID NO:2; k) a polypeptide consisting of the sequence of amino acid residues from residue 65 to residue 334 of SEQ ID NO:2; l) a polypeptide consisting of the sequence of amino acid residues from residue 65 to residue 847 of SEQ ID NO:2; m) a polypeptide consisting of the sequence of amino acid residues from residue 134 to residue 250 of SEQ ID NO:2; n) a polypeptide consisting of the sequence of amino acid residues from residue 134 to residue 334 of SEQ ID NO:2; o) a polypeptide consisting of the sequence of amino acid residues from residue 134 to residue 432 of SEQ ID NO:2; p) a polypeptide consisting of the sequence of amino acid residues from residue 134 to residue 847 of SEQ ID NO:2; q) a polypeptide consisting of the sequence of amino acid residues from residue 175 to residue 334 of SEQ ID NO:2; r) a polypeptide consisting of the sequence of amino acid residues from residue 175 to residue 432 of SEQ ID NO:2; and s) a polypeptide consisting of the sequence of amino acid residues from residue 175 to residue 847 of SEQ ID NO:2.

The invention also provides an isolated polypeptide as described above, further comprising an affinity tag or binding domain.

Within another aspect the invention provides a fusion protein comprising a secretory signal sequence having the amino acid sequence of amino acid residues 1–20 of SEQ ID NO:2, wherein the secretory signal sequence is operably linked to an additional polypeptide.

The invention also provides a fusion protein consisting essentially of a first portion and a second portion joined by a peptide bond, the first portion comprising a polypeptide as described above; and the second portion comprising another polypeptide.

Within another aspect the invention also provides an isolated polynucleotide molecule that encodes a polypeptide as described above. Within one embodiment the polypeptide further comprises an affinity tag or binding domain.

The invention also provides an isolated polynucleotide molecule, wherein the polynucleotide molecule is a degenerate nucleotide sequence encoding a polypeptide as described above.

The invention further provides an isolated polynucleotide encoding a polypeptide having an amino acid sequence that is at least 70% identical to the amino acid sequence of SEQ ID NO:2, wherein the isolated polypeptide specifically binds with an antibody to which a polypeptide having the amino acid sequence of SEQ ID NO:2 specifically binds. Within one embodiment the isolated polypeptide has an amino acid sequence that is at least 80% identical to the amino acid sequence of SEQ ID NO:2. Within another embodiment the isolated polypeptide has an amino acid sequence that is at least 90% identical to the amino acid sequence of SEQ ID NO:2. Within yet another embodiment difference between the amino acid sequence and the corresponding amino acid sequence of SEQ ID NO:2 is due to one or more conservative amino acid substitutions. Within still another embodiment the amino acid percent identity is determined using a FASTA program with ktup=1, gap opening penalty=10, gap extension penalty=1, and substitution matrix=blosum62, with other parameters set as default.

The invention provides an isolated polynucleotide molecule comprising the nucleotide sequence of nucleotides 58 to 3006 of SEQ ID NO:1.

The invention also provides an isolated polynucleotide molecule of SEQ ID NO:1.

The invention further provides an isolated polynucleotide selected from the group consisting of: a) a polynucleotide consisting of nucleotides 58–117 of SEQ ID NO:1; b) a polynucleotide consisting of nucleotides 118–249 of SEQ ID NO:1; c) a polynucleotide consisting of nucleotides 250–456 of SEQ ID NO:1; d) a polynucleotide consisting of nucleotides 457–579 of SEQ ID NO:1; e) a polynucleotide consisting of nucleotides 580–810 of SEQ ID NO:1; f) a polynucleotide consisting of nucleotides 811–1059 of SEQ ID NO:1; g) a polynucleotide consisting of nucleotides 1060–1353 of SEQ ID NO:1; h)a polynucleotide consisting of nucleotides 1354–3006 of SEQ ID NO:1; i) a polynucleotide consisting of nucleotides 250–579 of SEQ ID NO:1; j) a polynucleotide consisting of nucleotides 250–810 of SEQ ID NO:1; k) a polynucleotide consisting of nucleotides 250–1059 of SEQ ID NO:1; l) a polynucleotide consisting of nucleotides 250–1353 of SEQ ID NO:1; m) a polynucleotide consisting of nucleotides 250–3006 of SEQ ID NO:1; n) a polynucleotide consisting of nucleotides 457–810 of SEQ ID NO:1; o) a polynucleotide consisting of nucleotides 457–1059 of SEQ ID NO:1; p) a polynucleotide consisting of nucleotides 457–1353 of SEQ ID NO:1; q) a polynucleotide consisting of nucleotides 457–3006 of SEQ ID NO:1; r) a polynucleotide consisting of nucleotides 580–1059 of SEQ ID NO:1; s) a polynucleotide consisting of nucleotides 580–1353 of SEQ ID NO:1; t) a polynucleotide consisting of nucleotides 580–3006 of SEQ ID NO:1; and u) a polynucleotide consisting of nucleotides 811–1353 of SEQ ID NO:1.

The invention also provides a polynucleotide encoding a fusion protein comprising a secretory signal sequence having the amino acid sequence of amino acid residues 1–20 of SEQ ID NO:2, wherein the secretory signal sequence is operably linked to an additional polypeptide.

Still further, the invention provides a polynucleotide molecule encoding a fusion protein consisting essentially of a first portion and a second portion joined by a peptide bond, the first portion comprising a polypeptide as described above; and the second portion comprising another polypeptide.

Within another aspect the invention provides an expression vector comprising the following operably linked elements: a transcription promoter; a polynucleotide molecule that encodes a polypeptide as described above; and a transcription terminator. Within one embodiment the expression vector further comprises a secretory signal sequence operably linked to the DNA segment. Within another embodiment the polynucleotide encodes a polypeptide covalently linked amino terminally or carboxy terminally to an affinity tag.

Within another aspect the invention provides a cultured cell into which has been introduced an expression vector comprising the following operably linked elements: a transcription promoter; a polynucleotide molecule that encodes a polypeptide as described above; and a transcription terminator, wherein the cultured cell expresses the polypeptide encoded by the polynucleotide segment.

Within still another aspect the invention provides a method of producing a polypeptide comprising: culturing a cell into which has been introduced an expression vector comprising the following operably linked elements: a transcription promoter; a polynucleotide molecule that encodes a polypeptide as described above; and a transcription terminator; whereby the cell expresses the polypeptide encoded by the polynucleotide segment; and recovering the expressed polypeptide.

Within another aspect the invention provides an antibody or antibody fragment that specifically binds to a polypeptide as described above. Within one embodiment the antibody is selected from the group consisting of: a) polyclonal antibody; b) murine monoclonal antibody; c) humanized antibody derived from b); and d)human monoclonal antibody. Within another aspect the antibody fragment is selected from the group consisting of F(ab'), F(ab), Fab', Fab, Fv, scFv, and minimal recognition unit. Within another embodiment is an anti-idiotype antibody that specifically binds to the antibody described above.

Within another aspect is provided a polypeptide as described above in combination with a pharmaceutically acceptable vehicle.

These and other aspects of the invention will become evident upon reference to the following detailed description of the invention.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Meth. Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' (SEQ ID NO:13) are 5'-TAGCTTgagtct-3' (SEQ ID NO:14) and 3'-gtcgacTACCGA-5' (SEQ ID NO:15).

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

A new member of the follistatin family of proteins, zfsta2, has been identified from a human hypothalamic library. The zfsta2 protein has a predicted molecular weight of about 86,000 Da and exhibits the characteristic amino terminal cysteine-rich follistatin domain (Hohenester et al., *EMBO J.* 16:3778–86, 1997) found in other follistatin family members such as follistatin related protein or FRP (Zwijsen et al., ibid.), SPARC, also known as osteonectin or BM-40 or the human ortholog of mouse TSC-36 (Lane and Sage, ibid.), agrin (Patthy and Nikolics, ibid.), hevin (Girard and Springer, ibid.), the Flik protein of chickens (Amthor et al., ibid.) and the rat brain protein SC1 (Mendis et al., ibid.).

The present invention is based in part upon the discovery of a novel DNA sequence that encodes a polypeptide having homology to the family of follistatins. The zfsta2 polynucleotide sequence is disclosed in SEQ ID NO:1 and encodes a multi-domain secreted protein of 847 amino acids (SEQ ID NO:2). Sequence analysis of a deduced amino acid sequence of zfsta2, as represented by SEQ ID NO:2, indicates the presence of a 20 amino acid residue signal sequence (amino acid residues 1–20 of SEQ ID NO:2, nucleotides 58–117 of SEQ ID NO:1), followed by a predominantly hydrophilic short linker domain that has no known homology (amino acid residues 21–64 of SEQ ID NO:2, nucleotides 118–249 of SEQ ID NO:1), a follistatin homology domain (amino acid residues 65–133 of SEQ ID NO:2, nucleotides 250–456 of SEQ ID NO:1), an alpha-helical linker region (amino acid residues 134–174 of SEQ ID NO:2, nucleotides 457–579 of SEQ ID NO:1), a calmodulin domain (amino acid residue 175–250 of SEQ ID NO:2, nucleotides 580–810 of SEQ ID NO:1), an I-set IG domain #1 (amino acid residues 251–334 of SEQ ID NO:2, nucleotides 811–1059 of SEQ ID NO:1), an I-set IG domain #2 (amino acid residues 335–432 of SEQ ID NO:2, nucleotides 1060–1353 of SEQ ID NO:1) and a C-terminal domain with no known homology (amino acid residues 433–847 of SEQ ID NO:2, nucleotides 1354–3006 of SEQ ID NO:1). Those skilled in the art will recognize that predicted domain boundaries are approximations based on primary sequence content, and may vary slightly; however, such estimates are generally accurate to within ±5 amino acid residues.

The follistatin homology domain is predicted to fold into a structure similar to that determined for the follistatin homology domain in SPARC (Swiss-Prot SPRC_HUMAN, PDB 1BMO, also known as BM-40 or osteonectin, Hohenester et al., 1997). This is a beta hairpin structure, followed by a small hydrophobic core of alpha/beta structure. Unlike SPARC, which is glycosylated at Asn99, there is no predicted glycosylation site in zfsta2. Based on the disulfide bonding pattern in SPARC, the disulfide pairings in zfsta2 are as follows: Cys65–Cys76, Cys70–Cys87, Cys89–Cys119, Cys93–Cys112, and Cys101–Cys133, of SEQ ID NO:2. The zfsta2 follistatin homology domain has 47% identity to the follistatin domain in human follistatin related protein (Swiss-Prot FRP_HUMAN); the mouse orthologue of this protein is known as TSC-36 (Swiss-Prot FRP_MOUSE).

The follistatin homology domain has substantial sequence similarity to the Kazal family (Bode and Huber., *Eur. J. Biochem.* 204, 433–51, 1992) of serine proteinase inhibitors. Serine proteinase inhibitors regulate the proteolytic activity of target proteinases by occupying the active site and thereby preventing occupation by normal substrates. Although serine proteinase inhibitors fall into several unrelated structural classes, they all possess an exposed loop (variously termed an "inhibitor loop", a "reactive core", a "reactive site", a "binding loop") which is stabilized by intermolecular interactions between residues flanking the binding loop and the protein core (Bode and Huber, ibid.).

Interaction between inhibitor and enzyme produces a stable complex which disassociates very slowly, producing either a virgin or a modified inhibitor which is cleaved at the scissile bond of the binding loop. Based on analogy with the crystal structures for the proteinase inhibitors PEC-60 (PDB 1PCE), and ovomucoid (PDB 1OVO), the putative proteinase binding site in the follistatin homology domain of zfsta2 comprises the amino acid residues Cys93 (P3), Lys94 (P2), Arg95 (P1), His96 (P1'), and Tyr97 (P2') of SEQ ID NO:2. The scissile bond of the binding loop will therefore reside between the P1 and P1' residues Arg95 and His96 of SEQ ID NO:2.

The calmodulin homology domain is predicted to fold into a structure similar to that determined for the EC (EF-hand calcium binding; calmodulin-like) domain in SPARC (Hohenester et al., *EMBO J.* 16:3778–86, 1997). Calmodulin (Swiss-Prot CALM_HUMAN, PDB 1CLI) is an alpha-helical protein which binds calcium ions through the loops of helix-loop-helix substructures known as EF hands. Calmodulin has two structurally similar regions, each containing two EF hands, linked by a connecting helical segment. As is used herein "calmodulin homology domain" is meant to describe one of these two regions. The calmodulin homology domain of zfsta2 is predicted to contain two EF hand motifs, and hence two suspected calcium ion binding sites. Based on motif analysis, the loops of these two EF hands are predicted to reside between Asp amino acid residue 188 and Leu, amino acid residue, 200 of SEQ ID NO:2, and between Asp, amino acid residue 226 and Phe, amino acid residue 238 of SEQ ID NO:2. The last residue of the EF hand loop is always hydrophobic: in zfsta2 these residues are Leu, amino acid residue 200 and Phe, amino acid residue 238 of SEQ ID NO:2. In terms of sequence homology, the calmodulin homology domain of zfsta2 has 24% identity at the amino acid level, to the double EF hand segment of human protein phosphatase PPEF-2 (GenBank accession AF023456). The zfsta2 calmodulin homology domain has no detectable sequence homology to the calmodulin domain of SPARC.

The second EF hand of the calmodulin domain of SPARC is stabilized by a disulfide bond spanning the EF hand loop. When the two Cys residues in this EF hand were mutated to Leu residues, a 100-fold decrease in calcium ion affinity was noted (Hohenester et al., *Nat. Struct. Biol.,* 3:67–73, 1996). The present application also provides a mutated form of zfsta2 where the second EF hand is stabilized by replacing Asp, amino acid residue 225 and Ala, amino acid residue 241 of SEQ ID NO:2, with cysteine residues. This mutated form may have higher calcium binding affinity.

Between the follistatin and calmodulin homology domains is a short segment, called the alpha-helical linker which may form a short linker peptide between the two segments. This linker is predicted to have an alpha helical structure from Glu, amino acid residue 144 through Glu, amino acid residue 166 of SEQ ID NO;2. At the C-terminus of this linker are three basic residues which could be the location of a proteolysis site. Processing at this site of the secreted protein would release domains B and C, containing the follistatin homology domain, from the rest of the protein.

Amino acid residue 140 (Cys, SEQ ID NO:2) of the alpha-helical linker peptide may form a disulfide bond with amino acid residue 216 (Cys, SEQ ID NO:2), which precedes the second EF hand in the calmodulin homology domain of zfsta2.

The I-set IG domains #1 and #2 of zfsta2 are predicted to fold into a structure similar to that determined for the telokin peptide (Swiss-Prot KMLS_HUMAN, PDB 1TLK). The telokin peptide falls into the class of immunoglobulins (Bork et al., *J. Mol. Biol.* 242:309–20, 1994) which are all beta proteins folding into a beta-sandwich like structure. These have two beta sheets comprising 3+4 beta strands. Furthermore, the telokin peptide has been sub-classified as an "I" set immunoglobulin (IG) domain. Other proteins with I set immunoglobulin domains include titin, vascular and neural cell adhesion molecules, and twitchin. In zfsta2 domains I-set IG #1 and #2 there may be two intra-domain disulfide bonds, one between cysteine residues 270 and 321 of SEQ ID NO:2 in I-set IG domain #1 and cysteine residues 362 and 413 of SEQ ID NO:2 in I-set IG domain #2.

The C-terminal domain of zfsta2 shows no recognizable sequence or structural similarity to any known protein. This segment may serve to anchor the protein to the extracellular matrix, or to the cell surface membrane.

Northern blot analysis of various human tissues resulted in a transcript of approximately 5 kb seen in brain, placenta and spinal cord. RNA Dot Blot analysis indicated expression in the cerebellum, occipital lobe and pituitary gland.

The results of chromosomal localization showed that zfsta2 maps 2.84 cR_3000 from the framework marker WI-5113 on the chromosome 4 WICGR radiation hybrid map. Proximal and distal framework markers were WI-5113 and CHLC.GATA4C05.17, respectively. The use of surrounding markers positions zfsta2 in the 4q28.3 region on the integrated LDB chromosome 4 map.

The present invention further provides polynucleotide molecules, including DNA and RNA molecules, encoding zfsta2 proteins. The polynucleotides of the present invention include the sense strand; the anti-sense strand; and the DNA as double-stranded, having both the sense and anti-sense strand annealed together by their respective hydrogen bonds. A representative DNA sequence encoding a zfsta2 protein is set forth in SEQ ID NO:1. DNA sequences encoding other zfsta2 proteins can be readily generated by those of ordinary skill in the art based on the genetic code. Counterpart RNA sequences can be generated by substitution of U for T.

Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the zfsta2 polypeptide of SEQ ID NO:2. Those skilled in the art will recognize that the degenerate sequence of SEQ ID NO:3 also provides all RNA sequences encoding SEQ ID NO:2 by substituting U for T. Thus, zfsta2 polypeptide-encoding polynucleotides comprising nucleotide 1 to nucleotide 2949 of SEQ ID NO:3 and their RNA equivalents are contemplated by the present invention. Table 1 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCI | GCN |
| Gly | G | GGA GGC GGG GGT | GGN |
| Asn | N | AAC AAT | AAY |
| Asp | D | GAC GAT | GAY |

TABLE 2-continued

| Amino Acid | One Letter Code | Codons | Degenerate Codon |
|---|---|---|---|
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | — | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1,other polynucleotide probes, primers, fragments and sequences recited herein or sequences complementary thereto. Polynucleotide hybridization is well known in the art and widely used for many applications, see for example, Sambrook et al., *Molecular Cloning: A Laboratory Manual, Second Edition,* Cold Spring Harbor, N.Y., 1989; Ausubel et al., eds., *Current Protocols in Molecular Biology,* John Wiley and Sons, Inc., NY, 1987; Berger and Kimmel, eds., Guide to Molecular Cloning Techniques, *Methods in Enzymology,* volume 152, 1987 and Wetmur, *Crit. Rev. Biochem. Mol. Biol.* 26:227–59, 1990. Polynucleotide hybridization exploits the ability of single stranded complementary sequences to form a double helix hybrid. Such hybrids include DNA-DNA, RNA-RNA and DNA-RNA.

Hybridization will occur between sequences which contain some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Hybridization buffers generally contain blocking agents such as Denhardt's solution (Sigma Chemical Co., St. Louis, Mo.), denatured salmon sperm DNA, milk powders (BLOTTO), heparin or SDS, and a $Na^+$ source, such as SSC (1×SSC: 0.15 M NaCl, 15 mM sodium citrate) or SSPE (1×SSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM-1 M $Na^+$. Premixed hybridization solutions are also available from commercial sources such as Clontech Laboratories (Palo Alto, Calif.) and Promega Corporation (Madison, Wis.) for use according to manufacturer's instruction. Addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

Stringent hybridization conditions encompass temperatures of about 5–25° C. below the thermal melting point ($T_m$) of the hybrid and a hybridization buffer having up to 1 M $Na^+$. Higher degrees of stringency at lower temperatures can be achieved with the addition of formamide which reduces the $T_m$ of the hybrid about 1° C. for each 1% formamide in the buffer solution. Generally, such stringent conditions include temperatures of 20–70° C. and a hybridization buffer containing up to 6×SSC and 0–50% formamide. A higher degree of stringency can be achieved at temperatures of from 40–70° C. with a hybridization buffer having up to 4×SSC and from 0–50% formamide. Highly stringent conditions typically encompass temperatures of 42–70° C. with a hybridization buffer having up to 1×SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions that influence the $T_m$ include, the size and base pair content of the polynucleotide probe, the ionic strength of the hybridization solution, and the presence of destabilizing agents in the hybridization solution. Numerous equations for calculating $T_m$ are known in the art, see for example (Sambrook et al., ibid.; Ausubel et al., ibid.; Berger and Kimmel, ibid. and Wetmur, ibid.) and are specific for DNA, RNA and DNA-RNA hybrids and polynucleotide probe sequences of varying length. Sequence analysis software such as Oligo 4.0 and Primer Premier, as well as sites on the Internet, are available tools for analyzing a given sequence and calculating $T_m$ based on user defined criteria. Such programs can also analyze a given sequence under defined conditions and suggest suitable probe sequences. Typically, hybridization of longer polynucleotide sequences, >50 bp, is done at temperatures of about 20–25° C. below the calculated $T_m$. For smaller probes, <50 bp, hybridization is typically carried out at the $T_m$ or 5–10° C. below. This allows for the maximum rate of hybridization for DNA-DNA and DNA-RNA hybrids.

As previously noted, the isolated polynucleotides of the present invention include DNA and RNA. Methods for preparing DNA and RNA are well known in the art. In general, RNA is isolated from a tissue or cell that produces large amounts of zfsta2 RNA. Such tissues and cells are identified by Northern blotting (Thomas, *Proc. Natl. Acad. Sci. USA* 77:5201, 1980), and include brain and spinal cord. Total RNA can be prepared using guanidinium isothiocyanate extraction followed by isolation by centrifugation in a CsCl gradient (Chirgwin et al., *Biochemistry* 18:52–94, 1979). Poly $(A)^+$ RNA is prepared from total RNA using the method of Aviv and Leder (*Proc. Natl. Acad. Sci. USA* 69:1408–12, 1972). Complementary DNA (cDNA) is prepared from poly$(A)^+$ RNA using known methods. In the alternative, genomic DNA can be isolated. Polynucleotides encoding zfsta2 polypeptides are then identified and isolated by, for example, hybridization or PCR.

A full-length clone encoding a zfsta2 polypeptide can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zfsta2, receptor fragments, or other specific binding partners.

The polynucleotides of the present invention can also be synthesized using automated equipment. The current method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. Gene synthesis methods are well known in the art. See, for example, Glick and Pasternak, *Molecular Biotechnology, Principles & Applications of Recombinant DNA,* ASM Press, Washington, D.C., 1994; Itakura et al., *Annu. Rev. Biochem.* 53: 323–56, 1984; and Climie et al., *Proc. Natl. Acad. Sci. USA* 87:633–7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are zfsta2 polypeptides from other mammalian species, including murine, porcine, ovine, bovine, canine, feline, equine, and other primate polypeptides. Orthologs of human zfsta2 can be cloned using information and compositions provided by the present invention in combination with conventional cloning techniques. For example, a cDNA can be cloned using mRNA obtained from a tissue or cell type that expresses zfsta2 as disclosed herein. Suitable sources of mRNA can be identified by probing Northern blots with probes designed from the sequences disclosed herein. A library is then prepared from mRNA of a positive tissue or cell line. A zfsta2-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zfsta2 sequence disclosed herein. Within an additional method, the cDNA library can be used to transform or transfect host cells, and expression of the cDNA of interest can be detected with an antibody to zfsta2 polypeptide. Similar techniques can also be applied to the isolation of genomic clones.

Those skilled in the art will recognize that the sequence disclosed in SEQ ID NO:1 represents a single allele of human zfsta2 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zfsta2 polypeptide are included within the scope of the present invention, as are polypeptides encoded by such cDNAs and mRNAs. Splice variants are known in the follistatin family, follistatin exists in at least three forms (32,000, 35,000 and 39,000 Da) due to alternative splicing. Allelic variants and splice variants of these sequences can be cloned by probing cDNA or genomic libraries from different individuals or tissues according to standard procedures known in the art.

The present invention also provides isolated zfsta2 polypeptides that are substantially homologous to the polypeptides of SEQ ID NO:2 and their orthologs. The term "substantially homologous" is used herein to denote polypeptides having 50%, preferably 60%, more preferably at least 80%, sequence identity to the sequences shown in SEQ ID NO:2 or their orthologs. Such polypeptides will more preferably be at least 90% identical, and most preferably 95% or more identical to SEQ ID NO:2 or its orthologs. Percent sequence identity is determined by conventional methods. See, for example, Altschul et al., *Bull. Math. Bio.* 48: 603–16, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{\left[\begin{array}{c}\text{length of the longer sequence plus the number of gaps introduced}\\ \text{into the longer sequence in order to align the two sequences}\end{array}\right]}\times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zfsta2. The FASTA algorithm is described by Pearson and Lipman, *Proc. Nat. Acad. Sci. USA* 85:2444, 1988, and by Pearson, *Meth. Enzymol.* 183:63, 1990.

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then re-scored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63, 1990.

FASTA can also be used to determine the sequence identity of nucleic acid molecules using a ratio as disclosed above. For nucleotide sequence comparisons, the ktup value can range between one to six, preferably from four to six.

The BLOSUM62 table is an amino acid substitution matrix derived from about 2,000 local multiple alignments of protein sequence segments, representing highly conserved regions of more than 500 groups of related proteins (Henikoff and Henikoff, *Proc. Natl. Acad. Sci. USA* 89:10915, 1992). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Conservative amino acid changes in a zfsta2 gene can be introduced by substituting nucleotides for the nucleotides recited in SEQ ID NO:1. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8–10 to 8–22; and McPherson (ed.), *Directed Mutagenesis: A Practical Approach* (IRL Press 1991)). To select for variants having the properties of the wild-type protein can be done using standard methods, such as the assays described herein. Alternatively, a variant zfsta2 polypeptide can be identified by the ability to specifically bind anti-zfsta2 antibodies.

Variant zfsta2 polypeptides or substantially homologous zfsta2 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20–25 residues, or an affinity tag. Polypeptides comprising affinity tags can further comprise a proteolytic cleavage site between the zfsta2 polypeptide and the affinity tag. Preferred such sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions. For example, a zfsta2 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zfsta2 polypeptide fusions can be expressed in genetically engineered cells to produce a variety of multimeric zfsta2 analogs. Auxiliary domains can be fused to zfsta2 polypeptides to target them to specific. cells, tissues, or macromolecules. For example, a zfsta2 polypeptide or protein could be targeted to a predetermined cell type by fusing a zfsta2 polypeptide to a ligand that specifically binds to a receptor on the surface of the target cell. In this way, polypeptides and proteins can be targeted for therapeutic or diagnostic purposes. A zfsta2 polypeptide can be fused to two or more moieties, such as an affinity tag for purification and a targeting domain. Polypeptide fusions can also comprise one or more cleavage sites, particularly between domains. See, Tuan et al., *Conn. Tiss. Res.* 34:1–9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for zfsta2 amino acid residues.

Essential amino acids in the polypeptides of the present invention can be identified according to procedures known in the art, such as site-directed mutagenesis or alanine-scanning mutagenesis (Cunningham and Wells, *Science* 244: 1081–5, 1989; Bass et al., *Proc. Natl. Acad. Sci. USA* 88:4498–502, 1991). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699–708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related follistatins.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zfsta2 DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed herein, one of ordinary skill in the art can identify and/or prepare a variety of polypeptide fragments or variants of SEQ ID NO:2 that retain the properties of the wild-type zfsta2 protein. Such polypeptide fragments may include the N-terminal region, the follistatin and/or calmodulin homology domains, I-set IG domains #1 and/or #2, the alpha-helical linker and the C-terminal region. Amino acid truncations or additions can also occur.

For any zfsta2 polypeptide, including variants and fusion proteins, one of ordinary skill in the art can readily generate a fully degenerate polynucleotide sequence encoding that variant using the information set forth in Tables 1 and 2 above.

The zfsta2 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual,* 2nd ed., Cold Spring Harbor Laboratory Press, Cold Spring Harbor, N.Y., 1989, and Ausubel et al., eds., *Current Protocols in Molecular Biology,* John Wiley and Sons, Inc., NY, 1987.

In general, a DNA sequence encoding a zfsta2 polypeptide is operably linked to other genetic elements required for its expression, generally including a transcription promoter and terminator, within an expression vector. The vector will also commonly contain one or more selectable markers and one or more origins of replication, although. those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zfsta2 polypeptide into the secretory pathway of a host cell, a secretory signal sequence (also known as a leader sequence, prepro sequence or pre sequence) is provided in the expression vector. The secretory signal sequence may be that of zfsta2, or may be derived from another secreted protein (e.g., t-PA) or synthesized de novo. The secretory signal sequence is operably linked to the zfsta2 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residues 1–20 of SEQ ID NO:2 is be operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–5, 1982), DEAE-dextran mediated transfection (Ausubel et al., ibid.), and liposome-mediated transfection (Hawley-Nelson et al., Focus 15:73, 1993; Ciccarone et al., *Focus* 15:80, 1993, and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (*Bangalore*) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding the zfsta2 polypeptide is inserted into the baculoviral genome in place of the AcNPV polyhedrin gene coding sequence by one of two methods. The first is the traditional method of homologous DNA recombination between wild-type AcNPV and a transfer vector containing the zfsta2 flanked by AcNPV sequences. Suitable insect cells, e.g. SF9 cells, are infected with wild-type AcNPV and transfected with a transfer vector comprising a zfsta2 polynucleotide operably linked to an AcNPV polyhedrin gene promoter, terminator, and flanking sequences. See, King and Possee, *The Baculovirus Expression System: A Laboratory Guide,* London, Chapman & Hall; O'Reilly et al., *Baculovirus Expression Vectors: A Laboratory Manual,* New York, Oxford University Press., 1994; and, Richardson, Ed., *Baculovirus Expression Protocols. Methods in Molecular Biology,* Totowa, N.J., Humana Press, 1995. Natural recombination within an insect cell will result in a recombinant baculovirus which contains zfsta2 driven by the polyhedrin promoter. Recombinant viral stocks are made by methods commonly used in the art.

The second method of making recombinant baculovirus utilizes a transposon-based system described by Luckow (Luckow et al., *J. Virol.* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zfsta2 polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zfsta2. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins and Possee, *J. Gen. Virol.* 71:971–6, 1990; Bonning et al., *J. Gen. Virol.* 75:1551–6, 1994; and, Chazenbalk, G. D., and Rapoport, *J. Biol. Chem.* 270:1543–9, 1995. In such transfer vector constructs, a short or long version of the basic protein promoter can be used. Moreover, transfer vectors can be constructed which replace the native zfsta2 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native secretory signal sequence. In addition, transfer vectors can include an in-frame fusion with DNA encoding an epitope tag at the C- or N-terminus of the expressed zfsta2 polypeptide, for example, a Glu-Glu epitope tag (Grussenmeyer et al., ibid.). Using a technique known in the art, a transfer vector containing zfsta2 is transformed into *E. coli,* and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zfsta2 is subsequently produced. Recombinant viral stocks are made by methods commonly used the art.

The recombinant virus is used to infect host cells, typically a cell line derived from the fall armyworm, *Spodoptera frugiperda.* See, in general, Glick and Pasternak, *Molecular Biotechnology: Principles and Applications of Recombinant DNA,* ASM Press, Washington, D.C., 1994. Another suitable cell line is the High FiveO™ cell line (Invitrogen) derived from Trichoplusia ni (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the T. ni cells. The cells are grown up from an inoculation density of approximately 2–5×$10^5$ cells to a density of 1–2×$10^6$ cells at which time a recombinant viral stock is added at a multiplicity of infection (MOI) of 0.1 to 10, more typically near 3. The recombinant virus-infected cells typically produce the recombinant zfsta2 polypeptide at 12–72 hours post-infection and secrete it with varying efficiency into the medium. The culture is usually harvested 48 hours post-infection. Centrifugation is used to separate the cells from the medium (supernatant). The supernatant containing the zfsta2 polypeptide is filtered through micropore filters, usually 0.45 $\mu$m pore size. Procedures used are generally described in available laboratory manuals (King and Possee, ibid.; O'Reilly et al., ibid.; Richardson, C. D., ibid.). Subsequent purification of the zfsta2 polypeptide from the supernatant can be achieved using methods described herein.

Fungal cells, including yeast cells, can also be used within the present invention. Yeast species of particular interest in this regard include *Saccharomyces cerevisiae, Pichia pastoris,* and *Pichia methanolica.* Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11–23, 1998, and in WIPO Publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica,* it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\tau$) of from 1 to 40 milliseconds, most preferably about 20 milliseconds.

Prokaryotic host cells, including strains of the bacteria *Escherichia coli,* Bacillus and other genera are also useful host cells within the present invention. Techniques for transforming these hosts and expressing foreign DNA sequences cloned therein are well known in the art (see, e.g., Sambrook et al., ibid.). When expressing a zfsta2 polypeptide in bacteria such as *E. coli,* the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (see Garnier et al., *Cytotechnol.* 15:145–55, 1994). With either protocol, an expressed, secreted heterologous protein can be repeatedly isolated from the cell culture supernatant. Within the infected 293 cell production protocol, non-secreted proteins may also be effectively obtained.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zfsta2 polypeptides (or chimeric zfsta2 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods,* Pharmacia LKB Biotechnology, Uppsala, Sweden, 1988.

The polypeptides of the present invention can be isolated by exploitation of physical properties of the zfsta2 sequence or properties of coupled tags or epitopes. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.,* Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, FLAG tag, Glu-Glu tag, an immunoglobulin domain) may be constructed to facilitate purification. An exemplary purification method of protein constructs having an N-terminal or C-terminal affinity tag involves using an antibody to the affinity tag epitope to purify the protein using chromatography methods known in the art. SDS-PAGE, Western analysis, amino acid analysis and N-terminal sequencing can be done to confirm the identity of the purified protein.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Proteins/polypeptides which bind zfsta2 (such as a zfsta2-binding receptor) can also be used for purification of zfsta2. The zfsta2-binding protein/polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing zfsta2 polypeptide are passed through the column one or more times to allow zfsta2 polypeptide to bind to the ligand-binding or receptor polypeptide. The bound zfsta2 polypeptide is then eluted using changes in salt concentration, chaotropic agents (guanidine HCl), or pH to disrupt ligand-receptor binding.

Moreover, using methods described in the art, polypeptide fusions, or hybrid zfsta2 proteins, are constructed using regions or domains of the inventive zfsta2 in combination with other polypeptides, in particular, those of other follistatin family proteins (e.g. FRP, SPARC, agrin or hevin), or heterologous proteins (Sambrook et al., ibid., Altschul et al., ibid., Picard, *Cur. Opin. Biology,* 5:511–5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a domain(s) conferring a biological function may be swapped between zfsta2 of the present invention with the functionally equivalent domain(s) from another family member, such as FRP. Such domains include, but are not limited to, the secretory signal sequence, follistatin homology domain, calmodulin homology domain, I-set IG domains #1 and #2, the N or C-terminal domains and the alpha helical linker, for example. Such fusion proteins would be expected to have a biological functional profile that is the same or similar to polypeptides of the present invention or other known follistatin family proteins described herein, depending on the fusion constructed. Moreover, such fusion proteins may exhibit other properties as disclosed herein.

zfsta2 polypeptides or fragments thereof may also be prepared through chemical synthesis. zfsta2 polypeptides may be monomers or multimers; glycosylated or non-glycosylated; pegylated or non-pegylated; and may or may not include an initial methionine amino acid residue. Polypeptides, especially polypeptides of the present invention, can also be synthesized as described by Merrifield, *J. Am. Chem. Soc.* 85:2149, 1963, Stewart et al., "Solid Phase Peptide Synthesis" (2nd Edition), (Pierce Chemical Co., Rockford, Ill., 1984) and Bayer & Rapp *Chem. Pept. Prot.* 3:3, 1986 and Atherton et al., Solid Phase Peptide Synthesis: *A Practical Approach,* IRL Press, Oxford, 1989, for example.

As described above, the disclosed polypeptides can be used to construct zfsta2 variants and functional fragments of zfsta2. Such variants and extracellular domain fragments are considered to be zfsta2 agonists. Another type of zfsta2 agonist is provided by anti-idiotype antibodies, and fragments thereof, which mimic the extracellular domain of zfsta2. Moreover, recombinant antibodies comprising anti-idiotype variable domains that mimic the zfsta2 extracellular domain can be used as agonists (see, for example, Monfardini et al., *Proc. Assoc. Am. Physicians* 108:420, 1996). zfsta2 agonists can also be constructed using combinatorial libraries. Methods for constructing and screening phage display and other combinatorial libraries are provided, for example, by Kay et al., *Phase Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

The invention also provides antagonists, which either bind to zfsta2 polypeptides or, alternatively, to a receptor to which zfsta2 polypeptides bind, thereby inhibiting or eliminating the function of zfsta2. Such zfsta2 antagonists would include antibodies; oligonucleotides which bind either to the zfsta2 polypeptide or to its receptor; natural or synthetic analogs of zfsta2 polypeptides which retain the ability to bind the receptor but do not result in either ligand or receptor signaling. Such analogs could be peptides or peptide-like compounds. Natural or synthetic small molecules which bind to receptors of zfsta2 polypeptides and prevent signaling are also contemplated as antagonists. As such, zfsta2 antagonists would be useful as therapeutics for treating certain disorders where blocking signal from either a zfsta2 ligand or receptor would be beneficial. zfsta2 can also be used to identify inhibitors (antagonists) of its activity. Test compounds are added to the assays disclosed herein to identify compounds that inhibit the activity of zfsta2. In addition to those assays disclosed herein, samples can be tested for inhibition of zfsta2 activity within a variety of assays designed to measure receptor binding or the stimulation/inhibition of zfsta2-dependent cellular responses. For example, zfsta2-responsive cell lines can be transfected with a reporter gene construct that is responsive to a zfsta2-stimulated cellular pathway. Reporter gene constructs of this type are known in the art, and will generally comprise a zfsta2-DNA response element operably linked to a gene encoding an assayable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. Candidate compounds, solutions, mixtures or extracts are tested for the ability to inhibit the activity of zfsta2 on the target cells as evidenced by a decrease in zfsta2 stimulation of reporter gene expression. Assays of this type will detect compounds that directly block zfsta2 binding to cell-surface receptors, as well as compounds that block processes in the cellular pathway subsequent to receptor-ligand binding. In the alternative, compounds or other samples can be tested for direct blocking of zfsta2 binding to receptor using zfsta2 tagged with a detectable label (e.g., $^{125}I$, biotin, horseradish peroxidase, FITC, and the like). Within assays of this type, the ability of a test sample to inhibit the binding of labeled zfsta2 to the receptor is indicative of inhibitory activity, which can be confirmed through secondary assays. Receptors used within binding assays may be cellular receptors or isolated, immobilized receptors.

The invention also provides isolated and purified zfsta2 polynucleotide probes and/or primers. The probes and/or primers can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotide probes can be used when a small region of the gene is targeted for analysis. For gross analysis of genes, a polynucleotide probe may comprise an entire exon or more.

Such probes can also be used in hybridizations to detect the presence or quantify the amount of zfsta2 gene or mRNA transcript in a sample. zfsta2 polynucleotide probes could be used to hybridize to DNA or RNA targets for diagnostic purposes, using such techniques such as fluorescent in situ hybridization (FISH) or immunohistochemistry. Polynucleotide probes could be used to identify genes encoding zfsta2-like proteins. Such probes can also be used to screen libraries for related zfsta2 sequences. Such screening would be carried out under conditions of lower stringency which would allow identification of sequences which are substantially homologous, but not requiring complete homology to the probe sequence. Such methods and conditions are well known in the art, see, for example, Sambrook et al., *Molecular Cloning: A Laboratory Manual,* Second Edition, Cold Spring Harbor, N.Y., 1989. Such stringency conditions are described herein. Libraries may be made of genomic DNA or cDNA. Polynucleotide probes are also useful for Southern, Northern, or slot blots, colony and plaque hybridization and in situ hybridization. Mixtures of different zfsta2 polynucleotide probes can be prepared which would increase sensitivity or the detection of low copy number targets, in screening systems.

Nucleic acid molecules can be used to detect the expression of a zfsta2 gene in a biological sample. In a basic assay, a single-stranded probe molecule is incubated with RNA, isolated from a biological sample, under conditions of temperature and ionic strength that promote base pairing between the probe and target zfsta2 RNA species. After separating unbound probe from hybridized molecules, the amount of hybrids is detected.

A method of detecting the presence of zfsta2 RNA in a biological sample is provided, comprising the steps of:

a) contacting a zfsta2 nucleic acid probe under stringent hybridizing conditions with either
   i) test RNA molecules isolated from the biological sample, or
   ii) nucleic acid molecules synthesized from the isolated RNA molecules, wherein the probe has a nucleotide sequence comprising a portion of the nucleotide sequence of SEQ ID NOs:1 or 3, or their complements, and b) detecting the formation of hybrids of the nucleic acid probe and either the test RNA molecules or the synthesized nucleic acid molecules, wherein the presence of the hybrids indicates the presence of zfsta2 RNA is the biological sample.

Well-established hybridization methods of RNA detection include northern analysis and dot/slot blot hybridization (see, for example, Ausubel ibid. at pages 4–1 to 4–27, and Wu et al. (eds.), "Analysis of Gene Expression at the RNA Level," in *Methods in Gene Biotechnology,* pages 225–39, CRC Press, Inc., 1997). Nucleic acid probes can be detectably labeled with radioisotopes such as $^{32}$p or $^{35}$S. Alternatively, zfsta2 RNA can be detected with a nonradioactive hybridization method (see, for example, Isaac (ed.), *Protocols for Nucleic Acid Analysis by Nonradioactive Probes,* Humana Press, Inc., 1993). Typically, nonradioactive detection is achieved by enzymatic conversion of chromogenic or chemiluminescent substrates. Illustrative non-radioactive moieties include biotin, fluorescein, and digoxigenin.

zfsta2 oligonucleotide probes are also useful for in vivo diagnosis. As an illustration, $^{18}$F-labeled oligonucleotides can be administered to a subject and visualized by positron emission tomography (Tavitian et al., *Nat. Med.* 4:467, 1998).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics,* Humana Press, Inc., 1991; White (ed.), PCR Protocols: *Current Methods and Applications,* Humana Press, Inc., 1993; Cotter (ed.), *Molecular Diagnosis of Cancer,* Humana Press, Inc., 1996; Hanausek and Walaszek (eds.), *Tumor Marker Protocols,* Humana Press, Inc., 1998; Lo (ed.), *Clinical Applications of PCR,* Humana Press, Inc., 1998 and Meltzer (ed.), *PCR in Bioanalysis,* Humana Press, Inc., 1998). PCR primers can be designed to amplify a sequence encoding a particular zfsta2 region, such as the follistatin homology domain, encoded by about nucleotide 250 to nucleotide 456 of SEQ ID NO:1, and the calmodulin domain, encoded by about nucleotide 580 to nucleotide 810 of SEQ ID NO:1.

One variation of PCR for diagnostic assays is reverse transcriptase-PCR (RT-PCR). In the RT-PCR technique, RNA is isolated from a biological sample, reverse transcribed to cDNA, and the cDNA is incubated with zfsta2 primers (see, for example, Wu et al. (eds.), "Rapid Isolation of Specific cDNAs or Genes by PCR," in *Methods in Gene Biotechnology,* pages 15–28, CRC Press, Inc. 1997). PCR is then performed and the products are analyzed using standard techniques.

As an illustration, RNA is isolated from a biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or zfsta2 anti-sense oligomers. Oligo-dT primers offer the advantage that various mRNA nucleotide sequences are amplified that can provide control target sequences. zfsta2 sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled zfsta2 probe, and examined by autoradiography. Additional alternative approaches include the use of digoxigenin-labeled deoxyribonucleic acid triphosphates to provide chemiluminescence detection, and the C-TRAK colorimetric assay.

Another approach is real time quantitative PCR (Perkin-Elmer Cetus, Norwalk, Conn.). A fluorogenic probe, consisting of an oligonucleotide with both a reporter and a quencher dye attached, anneals specifically between the forward and reverse primers. Using the 5' endonuclease activity of Taq DNA polymerase, the reporter dye is separated from the quencher dye and a sequence-specific signal is generated and increases as amplification increases. The fluorescence intensity can be continuously monitored and quantified during the PCR reaction.

Another approach for detection of zfsta2 expression is cycling probe technology (CPT), in which a single-stranded DNA target binds with an excess of DNA-RNA-DNA chimeric probe to form a complex, the RNA portion is cleaved with RNase H, and the presence of cleaved chimeric probe is detected (see, for example, Beggs et al., *J. Clin. Microbiol.* 34:2985, 1996 and Bekkaoui et al., *Biotechniques* 20:240, 1996). Alternative methods for detection of zfsta2 sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161, 1996; Ehricht et al., *Eur. J. Biochem.* 243:358, 1997; and Chadwick et al., *J. Virol. Methods* 70:59, 1998). Other standard methods are known to those of skill in the art.

Zfsta2 probes and primers can also be used to detect and to localize zfsta2 gene expression in tissue samples. Methods for such in situ hybridization are well-known to those of skill in the art (see, for example, Choo (ed.), *In Situ Hybridization Protocols,* Humana Press, Inc., 1994; Wu et al. (eds.), "Analysis of Cellular DNA or Abundance of mRNA by Radioactive In Situ Hybridization (RISH)," in *Methods in Gene Biotechnology,* pages 259–278, CRC Press, Inc., 1997; and Wu et al. (eds.), "Localization of DNA or Abundance of mRNA by Fluorescence In Situ Hybridization (RISH)," in *Methods in Gene Biotechnology,* pages 279–289, CRC Press, Inc., 1997).

Various additional diagnostic approaches are well-known to those of skill in the art (see, for example, Mathew (ed.), *Protocols in Human Molecular Genetics,* Humana Press, Inc., 1991; Coleman and Tsongalis, *Molecular Diagnostics,* Humana Press, Inc., 1996; and Elles, *Molecular Diagnosis of Genetic Diseases,* Humana Press, Inc., 1996).

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

Probes and primers generated from the sequences disclosed herein can be used to map the zfsta2 gene to human chromosome 4. Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Radiation hybrid mapping panels are commercially available which cover the entire human genome, such as the Stanford G3 RH Panel and the GeneBridge 4 RH Panel (Research Genetics, Inc., Huntsville, Ala.). These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Sequence tagged sites (STSs) can also be used independently for chromosomal localization. An STS is a DNA sequence that is unique in the human genome and can be used as a reference point for a particular chromosome or region of a chromosome. An STS is defined by a pair of oligonucleotide primers that are used in a polymerase chain reaction to specifically detect this site in the presence of all other genomic sequences. Since STSs are based solely on DNA sequence they can be completely described within an electronic database, for example, Database of Sequence Tagged Sites (dbSTS), GenBank, (National Center for Biological Information, National Institutes of Health, Bethesda, MD http://www.ncbi.nlm. nih.gov), and can be searched with a gene sequence of interest for the mapping data contained within these short genomic landmark STS sequences.

The present invention also contemplates use of such chromosomal localization for diagnostic applications. Briefly, the zfsta2 gene, a probe comprising zfsta2 DNA or RNA or a subsequence thereof, can be used to determine if the zfsta2 gene is present on human chromosome 4 or if a mutation has occurred. Detectable chromosomal aberrations at the zfsta2 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255–65, 1995).

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, PCR Methods and Applications 1:34–8, 1991).

The invention also provides anti-zfsta2 antibodies. Antibodies to zfsta2 can be obtained, for example, using as an antigen the product of a zfsta2 expression vector, or zfsta2 isolated from a natural source. Particularly useful anti-zfsta2 antibodies "bind specifically" with zfsta2. Antibodies are considered to be specifically binding if the antibodies bind to a zfsta2 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660, 1949). Suitable antibodies include antibodies that bind with zfsta2 in particular domains, such as the zfsta2 follistatin homology domain (amino acid residues 65 to about 133 of SEQ ID NO:2), the calmodulin homology domain (located at about amino acid residues 175 to 250 of SEQ ID NO:2), or I-set IG domains #1 or #2 (located at about amino acid residues 251 to 334 of SEQ ID NO:2 or amino acid residues 335 to 432 of SEQ ID NO:2).

Anti-zfsta2 antibodies can be produced using antigenic zfsta2 epitope-bearing peptides and polypeptides. Antigenic epitope-bearing peptides and polypeptides of the present invention contain a sequence of at least nine, preferably between 15 to about 30 amino acids contained within SEQ ID NO:2. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with zfsta2. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

Polyclonal antibodies to recombinant zfsta2 protein or to zfsta2 isolated from natural sources can be prepared using methods well-known to those of skill in the art. See, for example, Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning* 2: *Expression Systems,* 2nd Edition, Glover et al. (eds.), page 15 (Oxford University Press 1995). The immunogenicity of a zfsta2 polypeptide can be increased through the use of an adjuvant, such as alum (aluminum hydroxide) or Freund's complete or incomplete adjuvant. Polypeptides useful for immunization also include fusion polypeptides, such as fusions of zfsta2 or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, hamsters, guinea pigs, goats or sheep, an anti-zfsta2 antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310, 1990. Antibodies can also be raised in transgenic animals such as transgenic sheep, cows, goats or pigs, and may be expressed in yeast and fungi in modified forms as will as in mammalian and insect cells.

Alternatively, monoclonal anti-zfsta2 antibodies can be generated. Rodent monoclonal antibodies to specific antigens may be obtained by methods known to those skilled in the art (see, for example, Kohler et al., Nature 256:495 (1975), Coligan et al. (eds.), *Current Protocols in Immunology,* Vol. 1, pages 2.5.1–2.6.7 (John Wiley & Sons 1991), Picksley et al., "Production of monoclonal antibodies against proteins expressed in *E. coli,*" in *DNA Cloning* 2: *Expression Systems, 2nd Edition,* Glover et al. (eds.), page 93 (Oxford University Press 1995)).

Briefly, monoclonal antibodies can be obtained by injecting mice with a composition comprising a zfsta2 gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-zfsta2 antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nat. Genet.* 7:13, 1994, Lonberg et al., *Nature* 368:856, 1994, and Taylor et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology,* Vol. 10, pages 79–104 (The Humana Press, Inc. 1992)).

For particular uses, it may be desirable to prepare fragments of anti-zfsta2 antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230, 1960, Porter, *Biochem. J.* 73:119, 1959, Edelman et al., in *Methods in Enzymology* Vol. 1, page 422 (Academic Press 1967), and by Coligan, ibid.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659, 1972. Alternatively, the variable chains can be linked by an intermolecular disulfide bond or cross-linked by chemicals such as gluteraldehyde (see, for example, Sandhu, *Crit. Rev. Biotech.* 12:437, 1992).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli.* The recombinant host cells synthesize a single polypeptide chain with a linker peptide bridging the two V domains. Methods for producing scFvs are described, for example, by Whitlow et al., *Methods: A Companion to Methods in Enzymology* 2:97, 1991, also see, Bird et al., *Science* 242:423, 1988, Ladner et al., U.S. Pat. No. 4,946,778, Pack et al., *Bio/Technology* 11:1271, 1993, and Sandhu, supra.

As an illustration, a scFV can be obtained by exposing lymphocytes to zfsta2 polypeptide in vitro, and selecting antibody display libraries in phage or similar vectors (for instance, through use of immobilized or labeled zfsta2 protein or peptide). Genes encoding polypeptides having potential zfsta2 polypeptide binding domains can be obtained by screening random peptide libraries displayed on phage (phage display) or on bacteria, such as *E. coli.* Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the zfsta2 sequences disclosed herein to identify proteins which bind to zfsta2.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991), Courtenay-Luck, "Genetic Manipulation of Monoclonal Antibodies," in *Monoclonal Antibodies: Production, Engineering and Clinical Application,* Ritter et al. (eds.), page 166 (Cambridge University Press 1995), and Ward et al., "Genetic Manipulation and Expression of Antibodies," in *Monoclonal Antibodies: Principles and Applications,* Birch et al., (eds.), page 137 (Wiley-Liss, Inc. 1995)).

Alternatively, an anti-zfsta2 antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989. Techniques for producing humanized monoclonal antibodies are described, for example, by Jones et al., *Nature* 321:522, 1986, Carter et al., *Proc. Nat'l Acad. Sci. USA* 89:4285, 1992, Sandhu, *Crit. Rev. Biotech.* 12:437, 1992, Singer et al., *J. Immun.* 150:2844, 1993, Sudhir (ed.), *Antibody Engineering Protocols* (Humana Press, Inc. 1995), Kelley, "Engineering Therapeutic Antibodies," in *Protein Engineering: Principles and Practice,* Cleland et al. (eds.), pages 399–434 (John Wiley & Sons, Inc. 1996), and by Queen et al., U.S. Pat. No. 5,693,762 (1997).

Polyclonal anti-idiotype antibodies can be prepared by immunizing animals with anti-zfsta2 antibodies or antibody fragments, using standard techniques. See, for example, Green et al., "Production of Polyclonal Antisera," in *Meth-*

*ods In Molecular Biology: Immunochemical Protocols,* Manson (ed.), pages 1–12 (Humana Press 1992). Also, see Coligan, ibid. at pages 2.4.1–2.4.7. Alternatively, monoclonal anti-idiotype antibodies can be prepared using anti-zfsta2 antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875, 1996.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zfsta2 polypeptides or anti-zfsta2 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

Expression of zfsta2 mRNA is largely confined to spinal cord, brain, and placenta with low level expression seen in a wide variety of other tissues. This is consistent with the reported distribution of follistatin gene transcripts and transcripts of a number of other follistatin family members. This distribution suggests that zfsta2 may play a role in neuron regeneration and repair within the CNS. Injury to the adult mammalian brain or spinal cord generates a cascade of cellular events leading to inflammation, proliferation of astrocytes, angiogenesis, and formation of a glial-mesodermal scar (Logan et al., *Brain Res.* 587:216–25, 1992; Wang et al., *Brain Res. Bull.* 36:607–9, 1995 and Lindholm et al., *J. Cell. Biol.* 117:395–400, 1992). Production of scar tissue within the CNS provides a physical barrier for regeneration of neurons and is thought to limit the ability of the adult CNS to recover after injury. Scar tissue formation in the CNS is thought to be dependent on the localized TGF-β stimulated production of extracellular matrix components, similar to what is seen for scar tissue formation in the periphery. Indeed, TGF-β mRNA and protein have been localized to astrocytes at the site of damage in the CNS (Logan et al., ibid., Wang et al., ibid. and Lindholm et al., ibid.) suggesting that a follistatin family member, such as zfsta2, facilitates neuron regeneration and establishment of new synaptic contacts by sequestering TGF-β. SC1, a member of the follistatin family, is expressed in brain astrocytes following injury (Mendis et al., *Brain Res.* 730:95–106, 1996) and follistatin related protein (FRP) is secreted by glioma cells in culture (Zwijsen et al., *Eur. J. Biochem.* 225:937–46, 1994).

Proteins that can sequester TGFβ and stimulate neuron regeneration would be useful in treatment of peripheral neuropathies by increasing spinal cord and sensory neurite outgrowth. Such polypeptides, agonists and antagonists can be included in therapeutic treatment to regenerate neurite outgrowths following strokes, brain damage caused by head injuries, and paralysis caused by spinal injuries. Application may also be made in treating neurodegenerative diseases such as Alzheimer's disease, Parkinson's disease and multiple sclerosis by stimulating neuronal outgrowths. Additional applications would include repair of transected axons which are common in lesions of multiple sclerosis.

Zfsta2 polypeptides, agonists or antagonists thereof may be therapeutically useful for treating brain and spinal cord injuries. To verify the presence of this capability in zfsta2 polypeptides, agonists or antagonists of the present invention, such zfsta2 polypeptides, agonists or antagonists are evaluated with respect to their ability to stimulate neuron regeneration and establish new synaptic contacts according to procedures known in the art, see for example Mendis et al., *Brain Res.* 730:95–106, 1996; Lindholm et al., *J. Cell Biol.* 117:395–400, 1992 and Logan et al., *Brain Res.* 587:216–25, 1992. If desired, zfsta2 polypeptide performance in this regard can be compared to other follistatins such as SC1 and FRP and the like. In addition, zfsta2 polypeptides or agonists or antagonists thereof may be evaluated in combination with one or more follistatins to identify synergistic effects. If desired, zfsta2 performance in this regard can be compared to other anti-inflammatory compounds, such as dexamethasone and hydrocortisone and the like.

In addition to its potential role in treatment of injuries to the CNS, zfsta2 may also have a role in host defense. Human marrow stromal cells have been shown to be reactive with anti-activin A antibodies and the production of the $B_A$-subunit mRNA is increased in these cells by a number of pro-inflammatory cytokines/regulators such as interleukin 1α, lipopolysaccaride, tumor necrosis factor-α, or 12-O-tetradecanoylphorbol 13-acetate (Shao et al., *Cytokine* 10:227–35, 1998). In contrast to the stimulatory effects of these agents, the anti-inflammatory compounds dexamethasone and hydrocortisone inhibited the constitutive and cytokine-stimulated expression of activin $B_A$-mRNA (Shao et al., ibid.).

Application of the polypeptides of the present invention may be made to inhibit inflammatory response, stimulate a reduction in the number and activity of inflammatory cells, and diminish edema and inflammation. Such anti-inflammatory polypeptides would find application in the treatment of acute inflammation conditions, bursitis, chronic inflammatory demyelinating polyneuropathy, various forms of contact dermatitis, contact vulvovaginitis, myositis, sepsis and ulcerative colitis. Use as therapeutic agents could also be made for treating acute renal failure, pancreatitis and neonatal bronchopulmonary dysplasia. Application can also be made for ocular injuries, such as corneal injury from burns or penetration of a foreign body or ocular inflammatory diseases such as uveitis.

Application may also be made to alleviate chronic itching and inflammation associated with dermatological conditions and skin diseases such as eczema, neurodermatitis, allergy, psoriasis, xerosis, insect bites, and burns, such as thermal, chemical and radiation burns, particularly sunburns.

Symptoms associated with gout, asthma, carpal tunnel syndrome, systemic lupus erythematosus, multiple sclerosis and myasthenia gravis may also be alleviated using the compounds of the present invention. zfsta2 polypeptide, agonist or antagonist-mediated removal of bioactive activin from sites of inflammation would be a useful therapy for treatment of a wide variety of inflammatory disorders. To verify the presence of this capability in zfsta2 polypeptides, or polypeptide fragments thereof, such polypeptides and polypeptide fragments are evaluated with respect to their ability to inhibit acute inflammation. Such methods are known in the art, in particular, zfsta2 polypeptides can be tested for anti-inflammatory activity in the carrageenan-induced rat footpad edema model (winter et al., *J. Pharmac. Exp. Ther.* 141:369–76, 1963 and Miele et al., *Nature* 335:726–30, 1988). Other models include the endotoxin-induced uveitis (EIU) model (Chan et al., *Arch. Ophthalmol.* 109:278–81, 1991), Oxazolone-induced inflammation model (Lloret and Moreno, *Biochem. Pharmocol.* 44:1437, 1992), croton oil-induced inflammation model, PMA-induced inflammation model (Miele et al., ibid.), and dextran-induced edema assay for anti-inflammatory agents (Ialenti et al., *Agents Actions* 29:48–9, 1990 and Rosa and Willoughby, *J. Pharm. Pharmac.* 23:297–8, 1971). Efficacy for treating diseases such as rheumatoid arthritis can be evaluated using indicators which would include a reduction in inflammation and relief of pain or stiffness, and in animal models indications would be derived from macroscopic inspection of joints and change in swelling of hind paws. If desired, zfsta2 polypeptide performance in this regard can be compared to other anti-inflammatory agents, in particular, dexamethasone and hydrocortisone. In addition, zfsta2 polypeptides may be evaluated in combination with one or more anti-inflammatory agents to identify synergistic effects.

The recent conformation of the sequence identity of erythroid differentiation factor (EDF) and $B_A$ subunit of activins and inhibins (Murata et al., *Proc. Natl. Acad. Sci. USA* 85:2434, 1988) suggests a role for zfsta2 in regulating hematopoiesis and differentiation of erythroid progenitors. EDF exhibits potent differentiation-inducing activity towards cultured erythroleukemia cells and enhances the growth of normal erythroid precursor cells in vitro and in vivo (Yu et al., *Nature,* 330:765, 1987, Shiozaki, et al., *Biochem. Biophys. Res. Commun.* 165:1155, 1989) and activin A/EDF is expressed in activated macrophages (Eramaa et al., *J. Exp. Med.* 176:1449–52, 1992). Continuous intraperitoneal administration of follistatin to normal mice resulted in a decrease of erythroid progenitors in bone marrow and spleen (Shiozaki et al., *Proc. Natl. Acad. Sci. USA* 89:1553–6, 1992) demonstrating that follistatin modulates murine erythropoeisis. In humans, moreover, the follistatin related gene is a target of chromosonal rearrangement in a B-cell chronic lymphocytic leukemia (Hayette et al., *Oncogene* 16:2949–54, 1998).

EDF-binding proteins such as zfsta2 polypeptides, agonists or antagonists would provide a useful therapeutic for modulating hematopoiesis and differentiation of erythroid progenitors. To verify the presence of this capability, zfsta2 polypeptides and agonists of the present invention are evaluated with respect to their ability to alter erythropoiesis by decreasing erythroid progenitors in bone marrow and spleen, according to procedures known in the art. zfsta2 antagonists can be evaluated with respect to enhancing hematopoiesis and differentiation of erythroid progenitors by inactivating follistatin and follistatin-like molecules. If desired, zfsta2 performance in this regard can be compared to other follistatins or hematopoietic factors such as erythropoietin or thrombopoietin and the like. In addition, zfsta2 polypeptides or agonists or antagonists thereof may be evaluated in combination with one or more follistatins to identify synergistic effects.

The pleiotropic actions of activins and inhibins on the gonadal/hypothalamic/pituitary axis would indicate that follistatins, such as zfsta2, would be useful in treatment of fertility disorders such characterized by abnormalities in hormone production. Activin A, for example, has been shown to stimulate hypothalamic oxytocin secretion (Sawchenko et al., *Nature* 334:615–7; 1988). Oxytocin specifically stimulates uterine contraction near term. Proteins which bind activin A would serve as useful therapeutics for delaying birth in pre-term pregnancies.

Folliculogenesis is a physiological event characterized by morphological and functional changes of the follicle. Of these events, antrum formation is considered the milestone of this pathway, a process that is governed by the pituitary hormone FSH. Since FSH is required for normal function of the ovaries, and activin is required for activation of FSH synthesis and secretion, it is not surprising that follistatin is an important regulator of ovarian function. Follistatin mRNA is present in primordial follicles and its levels are dramatically increased in granulosa cells of the growing secondary or tertiary follicles and then decreases in the pre-ovulatory follicles (Shimasaki et al., *Mol. Endocrinol.* 3:651–9, 1989). Recent in vitro assay systems have also shown that activin is directly folliculogenic in immature mice but not in adults, the inhibition of folliculogenesis in adults was, furthermore, reversed by follistatin (Yokota et al., *Endocrinology* 138:4572–6, 1997). The balance between activin and follistatin appears to be critical for normal ovarian function as overexpression of mouse follistatin in female transgenic mice had a number of reproductive defects (Guo et al., *Mol. Endocrinol.* 12: 96–106, 1998). Follistatins, such as zfsta2, play a role in regulating folliculogenesis by affecting proliferation or differentiation of follicular cells, affecting cell-cell interactions, modulating hormones involved in the process, and the like. The role of sex steroids, such as FSH, on target tissues and organs, e.g., uterus, breast, adipose, bones and liver, has made modulators of their activity desirable for therapeutic applications. Such applications include treatments for precocious puberty, endometriosis, uterine leiomyomata, hirsutism, infertility, pre-menstrual syndrome (PMS), amenorrhea, and as contraceptive agents.

The level and ratio of gonadotropin and steroid hormones in the blood can be used to assess the existence of hormonal imbalances associated with diseases, as well as determine whether normal hormonal balance has been restored after administration of a therapeutic agent. Determination of estradiol, progesterone, LH, and FSH levels, for example, from serum is known by one of skill in the art. Such assays can be used to monitor the effects on hormone levels after administration of zfsta2 in vivo, or in a transgenic mouse model where the zfsta2 gene is expressed or the murine ortholog is deleted.

The zfsta2 polypeptides, agonists and antagonists of the present invention may be used directly or incorporated into therapies for treating reproductive disorders. As a hormone-modulating molecule, zfsta2 polypeptides, agonists and antagonists can have therapeutic application for treating, for example, breakthrough menopausal bleeding, as part of a therapeutic regime for pregnancy support, or for treating symptoms associated with polycystic ovarian syndrome (PCOS), PMS and menopause. In addition, other in vivo rodent models are known in the art to assay effects of zfsta2 polypeptides, agonists and antagonists on, for example, polycystic ovarian syndrome (PCOS).

Activin, inhibin and follistatin are also found in the testes. mRNA encoding follistatin is located in many germ cells including type B spermatogonia, primary spermatocytes and spermatids at steps 1 to 11 (Meinhardt et al., *J. Reprod. Fertil.* 112:233–41, 1998). It is also found in Sertoli cells and endothelial cells but not in Leydig cells. Immunohistochemistry with anti-follistatin antibodies showed that the protein was localized to spermatids at all stages and it was also localized to endothelial and Leydig cells. This widespread localization, together with follistatin's capacity to neutralize the activity of activin, suggests that follistatin modulates spermatogenesis and a range of other testicular functions. The balance between activin and follistatin plays an important role in normal reproduction in males was shown in mouse follistatin transgenic mice: males exhibited variable degrees of Leydig cell hyperplasia, spermatogenesis was arrested, and seminiferous tubules degenerated which lead to infertility. This suggests that reproductive disorders due to an excess of activin or other TGF-beta family members would be amenable to treatment with members of the follistatin family. Additionally, follistatin antagonists would be useful in treatment regimes to enhance male fertility.

In vivo assays for evaluating the effect of zfsta2 polypeptides, agonists and antagonists on testes are well known in the art. For example, compounds can be injected intraperitoneally for a specific time duration. After the treatment period, animals are sacrificed and testes removed and weighed. Testicles are homogenized and sperm head counts are made (Meistrich et al., *Exp. Cell Res.* 99:72–78, 1976).

Other activities, for example, chemotaxic activity that may be associated with proteins of the present invention can be analyzed. For example, late stage factors in spermatogenesis may be involved in egg-sperm interactions and sperm motility. Activities, such as enhancing viability of cryopreserved sperm, stimulating the acrosome reaction, enhancing sperm motility and enhancing egg-sperm interactions may be associated with the proteins of the present invention. Assays evaluating such activities are known (Rosenberger, *J. Androl.* 11:89–96, 1990; Fuchs, *Zentralbl Gynakol* 11:117–120, 1993; Neurwinger et al., *Andrologia* 22:335–9, 1990; Harris et al., *Human Reprod.* 3:856–60, 1988; and Jockenhovel, *Andrologia* 22:171–178, 1990; Lessing et al., *Fertil. Steril.* 44:406–9 (1985); Zaneveld, In Male Infertility Chapter 11, Comhaire Ed., Chapman & Hall, London 1996). These activities are expected to result in enhanced fertility and successful reproduction.

zfsta2 polypeptides, agonists or antagonists would provide a useful therapeutic for modulating reproductive hormones. To verify the presence of this capability, zfsta2 polypeptides, agonists and antagonists of the present invention are evaluated with respect to their ability to regulate hormones associated with reproduction, according to procedures known in the art. For example, Guoqetal, *Mol. Endocrinol.* 12:96–106, 1998 describes RIA measurement of serum LH, FSH, testosterone, estradiol, activin and follistatin. Zfsta2 polypeptides and agonists would be useful for treating male and female reproductive disorders. Zfsta2 antagonists would also be useful as contraceptives. If desired, zfsta2 performance in this regard can be compared to other follistatins and the like. In addition, zfsta2 polypeptides or agonists or antagonists thereof may be evaluated in combination with one or more follistatins. to identify synergistic effects.

Zfsta2 polypeptides, agonists and antagonists of the present invention may also be used in applications for enhancing fertilization during assisted reproduction in humans and in animals. Such assisted reproduction methods are known in the art and include artificial insemination, in vitro fertilization, embryo transfer, and gamete intrafallopian transfer. Such methods are useful for assisting those who may have physiological or metabolic disorders that prevent or impede natural conception. Such methods are also used in animal breeding programs, e.g., for livestock, racehorses, domestic and wild animals, and could be used as methods for the creation of transgenic animals. Zfsta2 polypeptides, agonists or antagonists could be used in the induction of ovulation, either independently or in conjunction with a regimen of gonadotropins or agents such as clomiphene citrate or bromocriptine (Speroff et al., Induction of ovulation, *Clinical Gynecologic Endocrinology and Infertility,* $5^{th}$ ed., Baltimore, Williams & Wilkins, 1994). Zfsta2 polypeptides, agonists and antagonists can also be used in stimulation of spermatogenesis, independently or in conjunction with other gonadotropins or sex steroids such as testosterone. As such, proteins of the present invention can be administered to the recipient prior to fertilization or combined with the sperm, an egg or an egg-sperm mixture prior to in vitro or in vivo fertilization. Such proteins can also be mixed with oocytes or sperm prior to cryopreservation to enhance viability of the preserved tissues for use in assisted reproduction.

The formation of bone and teeth and is a multi-step process that is known to be initiated and promoted by members of the TGF-β superfamily, including TGF-βs and bone morphogenic proteins (BMPs). Accumulating evidence suggests that activin and follistatin play regulatory roles in both tooth and bone formation. The temporal-spatial expression of activin and follistatin in pre-odontoblasts suggests that activin is required for proliferation of these cells, while odontoblast terminal differentiation is mediated, at least partly, by follistatin inactivation of these proliferative effects (Heikinheimo et al., *J. Dent. Res.* 76:1625–36; 1997, Heikinheimo et al., *Eur. J. Oral Sci.* 106:167–73; 1998). Follistatin is also expressed in bone (Inoue et al., *Calcif. Tiss. Int.* 55:395–7, 1994) and activin and follistatin have been detected by immunohistochemistry in healing fractures in the rat (Nagamine et al., *J. Orthopaed. Res.* 16:314–21, 1998). Follistatin has also been detected in developing bone and the expression of follistatin and activin A genes during demineralized bone matrix-induced endochondral bone development suggests a cooperative interaction between follistatin and activin during bone formation (Funaba, et al., *Endocrinology* 137:4250–9, 1996).

Such therapeutic agents may be used for repair of bone defects and deficiencies, such as those occurring in closed, open and non-union fractures; prophylactic use in closed and open fracture reduction; promotion of bone healing in plastic surgery; stimulation of bone ingrowth into non-cemented prosthetic joints and dental implants; elevation of peak bone mass in pre-menopausal women; treatment of growth deficiencies; treatment of periodontal disease and defects, and other tooth repair processes; increase in bone formation during distraction osteogenesis; and treatment of other skeletal disorders, such as age-related osteoporosis, post-menopausal osteoporosis, glucocorticoid-induced osteoporosis, diabetes-associated osteoporosis or disuse osteoporosis and arthritis. The compounds of the present invention can also be useful in repair of congenital, trauma-induced or surgical resection of bone (for instance, for cancer treatment), and in cosmetic surgery. Further uses include limiting or treating cartilage defects or disorders and stimulation of wound healing and tissue repair.

Well established animal models are available to test in vivo efficacy of modulators of bone formation. For example, the hypocalcemic rat or mouse model can be used to determine the effect of test compounds on serum calcium, and the ovariectomized rat or mouse can be used as a model system for osteoporosis. Bone changes seen in these models and in humans during the early stages of estrogen deficiency are qualitatively similar.

Molecules that are capable of modulating the effects of members of the TGF-β family, such as zfsta2 polypeptides, agonists or antagonists, would provide molecules useful for tooth and bone formation. To verify the presence of this capability, zfsta2 polypeptides, agonists and antagonists of the present invention are evaluated with respect to their ability to stimulate tooth or bone formation according to procedures known in the art. If desired, zfsta2 performance in this regard can be compared to other follistatins and the like. In addition, zfsta2 polypeptides or agonists or antagonists thereof may be evaluated in combination with one or more follistatins. to identify synergistic effects.

Follistatin and activin also appear likely to play a role in the pathogenesis of atherosclerosis. In vascular wall cells, activin-A has been shown to inhibit endothelial cell growth and promote smooth muscle cell growth (Kojima et al., *Exp. Cell Res.* 206:152–6; 1993, McCarthy and Bicknell, *J. Biol. Chem.* 268:23066–71; 1993) and has been shown to produce a modest inhibition of scavenger receptor, SRB1, expression and foam cell formation in THP-1 macrophages (Kozaki et al., *Arterioscler. Thromb. Vasc. Biol.* 17:2389–94; 1997). These effects are antagonized by follistatin. Activin-A, follistatin and bone morphogenic protein-2, are produced by human atherosclerotic lesions and expression of the first two has been localized to the neointima of the diseased arteries (Inoue et al., *Biochem. Biophys. Res. Commun.* 205:441–8; 1994). These data suggest that the relative balance between activin, and its binding protein, follistatin, may be important in initiation and progression of atherosclerotic lesions.

Zfsta2 polypeptides, agonists or antagonists would be useful for neutralizing the activities of TGF-β family members. Such molecules would provide a novel therapy for treatment of restenosis after angioplasty. Additionally, TGF-β neutralizers would be useful for the treatment of atherosclerosis. Use of such molecules would also be applicable for treatment of stroke.

Follistatin and activin appear to play important roles in development. Two classes of TGF-β family members are believed to determine the dorsal/ventral pattern of the mesoderm in early development in *Xenopus laevi.* The first are related to activin and induce the formation of the dorsal mesoderm, which gives rise to muscle and the notocord (Asashima et al., *Roux's Arch. Dev. Biol.* 198:330–5, 1990) and the second are related to the bone morphogenic proteins (BMPs) which inhibit dorsal mesoderm formation and induce cells to take on ventral fates, such as blood cells (Maeno et al., *Dev. Biol.* 161: 522–9, 1994). Follistatin can block the activities of activin (Fukui et al., *Dev. Biol.* 159:131–9, 1993) and BMPs (Iemura et al., *Proc. Natl. Acad. Sci. USA* 95:9337–42, 1998) in these systems. Taken together, these findings suggest that zfsta2, as a member of the follistatin family of TGF-beta binding proteins, may useful as a therapy for a wide range of developmental disorders.

The effects of zfsta2 can be measured in vitro using cultured cells or in vivo by administering molecules of the claimed invention to the appropriate animal model. For instance, zfsta2 transfected or co-transfected expression host cells may be embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about $5\times10^5$ to about $5\times10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached). A large bore needle is then attached to the syringe, and the thread is intraperitoneally injected into a recipient in a minimal volume of the Lactated Ringer's Solution.

An alternative in vivo approach for assaying proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161–89, 1994; and Douglas and Curiel, *Science & Medicine* 4:44–53, 1997). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Polynucleotides encoding zfsta2 polypeptides are useful within gene therapy applications where it is desired to increase or inhibit zfsta2 activity. If a mammal has a mutated or absent zfsta2 gene, the zfsta2 gene can be introduced into the cells of the mammal. In one embodiment, a gene encoding a zfst2 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a zfsta2 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit zfsta2 gene transcription, such as to inhibit cell proliferation in vivo. Polynucleotides that are complementary to a segment of a zfsta2-encoding polynucleotide (e.g., a polynucleotide as set froth in SEQ ID NO:1) are designed to bind to zfsta2-encoding mRNA and to inhibit translation of such mRNA. Such antisense polynucleotides are used to inhibit expression of zfsta2 polypeptide-encoding genes in cell culture or in a subject.

Transgenic mice, engineered to express the zfsta2 gene, and mice that exhibit a complete absence of zfsta2 gene function, referred to as "knockout mice" (Snouwaert et al., *Science* 257:1083, 1992), may also be generated (Lowell et al., *Nature* 366:740–42, 1993). These mice may be employed to study the zfsta2 gene and the protein encoded thereby in an in vivo system.

The zfsta2 polypeptides are also contemplated for pharmaceutical use. Pharmaceutically effective amounts of zfsta2 polypeptides, agonists or zfsta2 antagonists of the present invention can be formulated with pharmaceutically acceptable carriers for parenteral, oral, nasal, rectal, topical, transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. Slow or extended-release delivery systems, including any of a number of biopolymers (biological-based systems), systems employing liposomes, and polymeric delivery systems, can also be utilized with the compositions described herein to provide a continuous or long-term source of the zfsta2 polypeptide or antagonist. Such slow release systems are applicable to formulations, for example, for oral, topical and parenteral use. The term "pharmaceutically acceptable carrier" refers to a carrier medium which does not interfere with the effectiveness of the biological activity of the active ingredients and which is not toxic to the host or patient. One skilled in the art may formulate the compounds of the present invention in an appropriate manner, and in accordance with accepted practices, such as those disclosed in *Remington's Pharmaceutical Sciences,* Gennaro (ed.), Mack Publishing Co., Easton, Pa. 1990.

As used herein a "pharmaceutically effective amount" of a zfsta2 polypeptide, agonist or antagonist is an amount sufficient to induce a desired biological result. The result can be alleviation of the signs, symptoms, or causes of a disease, or any other desired alteration of a biological system. For example, an effective amount of a zfsta2 polypeptide is that which provides either subjective relief of symptoms or an objectively identifiable improvement as noted by the clinician or other qualified observer. Effective amounts of the zfsta2 polypeptides can vary widely depending on the disease or symptom to be treated. The amount of the polypeptide to be administered and its concentration in the formulations, depends upon the vehicle selected, route of administration, the potency of the particular polypeptide, the clinical condition of the patient, the side effects and the stability of the compound in the formulation. Thus, the clinician will employ the appropriate preparation containing the appropriate concentration in the formulation, as well as the amount of formulation administered, depending upon clinical experience with the patient in question or with similar patients. Such amounts will depend, in part, on the particular condition to be treated, age, weight, and general health of the patient, and other factors evident to those skilled in the art. Typically a dose will be in the range of 0.1–100 mg/kg of subject. Doses for specific compounds may be determined from in vitro or ex vivo studies in combination with studies on experimental animals. Concentrations of compounds found to be effective in vitro or ex vivo provide guidance for animal studies, wherein doses are calculated to provide similar concentrations at the site of action.

The dosages of the present compounds used to practice the invention include dosages effective to result in the desired effects. Estimation of appropriate dosages effective for the individual patient is well within the skill of the ordinary prescribing physician or other appropriate health care practitioner. As a guide, the clinician can use conventionally available advice from a source such as the Physician's Desk Reference, $48^{th}$ Edition, Medical Economics Data Production Co., Montvale, N.J. 07645–1742 (1994).

Preferably the compositions are presented for administration in unit dosage forms. The term "unit dosage form" refers to physically discrete units suitable as unitary dosed for human subjects and animals, each unit containing a predetermined quantity of active material calculated to produce a desired pharmaceutical effect in association with the required pharmaceutical diluent, carrier or vehicle. Examples of unit dosage forms include vials, ampules, tablets, caplets, pills, powders, granules, eyedrops, oral or ocular solutions or suspensions, ocular ointments, and oil-in-water emulsions. Means of preparation, formulation and administration are known to those of skill, see generally Remington's ibid.

The invention is further illustrated by the following non-limiting examples.

EXAMPLES

Example 1

Extension of EST Sequence

The novel zfsta2 polypeptide-encoding polynucleotides of the present invention were initially identified by querying an EST database for follistatin homologs. An EST discovered and predicted to be related to the follistatin family, but lacked complete 5' and 3' regions. To identify the corresponding full length cDNA, a clone considered likely to contain the missing 3' coding region was used for sequencing. Using an Invitrogen S.N.A.P.™ Miniprep kit (Invitrogen, Corp., San Diego, Calif.) according to manufacturer's instructions a 5 ml overnight culture in LB+50 μg/ml ampicillin was prepared. The template was sequenced on an ABIPRISM™ model 377 DNA sequencer (Perkin-Elmer Cetus, Norwalk, Conn.) using the ABI PRISM™ Dye Terminator Cycle Sequencing Ready Reaction Kit (Perkin-Elmer Corp.) according to manufacturer's instructions. Sequencing reactions were carried out in a Hybaid OmniGene Temperature Cycling System (National Labnet Co., Woodbridge, N.Y.). SEQUENCHER™ 3.0 sequence analysis software (Gene Codes Corporation, Ann Arbor, Mich.) was used for data analysis. The resulting 1965 bp sequence provided the 3' end of the zfsta2 cDNA (SEQ ID NO:7).

Using fetal brain, brain, spinal cord and retina Marathon™ cDNA libraries (Clontech, Palo Alto, Calif.) as separate templates and oligonucleotide primer ZC18,415 (SEQ ID NO:5) to the initial EST and oligonucleotide primer ZC14701 (SEQ ID NO:6) to an internal sequence of zfsta2 from above, 5' RACE was carried out at 94° C., for 1.5 minutes, followed by 35 cycles at 94° C. for 5 seconds and 66° C. for 1.5 minutes, followed by a 10 minute extension at 72° C. A band of approximately 1255 bp (SEQ ID NO:8) was resolved by gel electrophoresis from each of the templates. 5' RACE fragments from each of the above reactions were ligated into a TA vector (Invitrogen Inc, San Diego, Calif.) according to manufacturer's instructions. The sequence of the 5' end of zfsta2 was confirmed from a fetal brain PCR fragment by sequence analysis as described above. The 3' EST-derived sequence and the 5' RACE-derived sequence were joined together through an overlapping sequence and the complete cDNA sequence of zfsta2 is disclosed in SEQ ID NO:1.

Example 2

Tissue Distribution

Human Multiple Tissue Northern Blots (MTN I, MTN II and MTN III; Clontech) were probed to determine the tissue distribution of human zfsta2 expression. An approximately 140 bp PCR derived probe (SEQ ID NO:4) was amplified using fetal brain, brain, spinal cord and retina Marathon™ cDNA libraries (Clontech) as templates and oligonucleotide ZC12881 (SEQ ID NO:9) and ZC12884 (SEQ ID NO:10) as primers. The amplification was carried out as follows: 1 cycle at 94° C. for 1.5 minutes, 35 cycles of 94° C. for 15 seconds and 60° C. 30 seconds, followed by 1 cycle at 72° C. for 10 minutes. The PCR products were visualized by agarose gel electrophoresis and the 140 bp PCR product from fetal brain was purified using a Gel Extraction Kit (Qiagen, Chatsworth, Calif.) according to manufacturer's instructions. The probe was radioactively labeled using the MULTIPRIME DNA labeling kit (Amersham, Arlington Heights, Ill.) according to the manufacturer's instructions. The probe was purified using a NUCTRAP push column (Stratagene). EXPRESSHYB (Clontech) solution was used for prehybridization and as a hybridizing solution for the Northern blots. Hybridization and washes were done under appropriately stringent conditions. A strong transcript of approximately 5 kb was seen in spinal cord and placenta, and a weaker transcript was detected in brain.

A RNA Master Dot Blot (Clontech) that contained RNAs from various tissues that were normalized to 8 housekeeping genes was also probed and hybridized as described above. Expression was seen in the cerebellum, occipital lobe and pituitary gland.

Example 3

Chromosomal Localization zfsta2 was mapped to chromosome 4 using the commercially available "GeneBridge 4Radiation Hybrid Panel" (Research Genetics, Inc.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MITCenter for Genome Research's radiation hybrid map of the human genome (the "WICGR" radiation hybrid map) which was constructed with the GeneBridge 4 Radiation Hybrid Panel.

For the mapping of zfsta2 with the GeneBridge 4 RH Panel, 20 μl reactions were set up in a 96-well microtiter plate (Stratagene, La Jolla, Calif.) and used in a "RoboCycler Gradient 96" thermal cycler (Stratagene). Each of the 95 PCR reactions consisted of 2 μl 10×PCR reaction buffer (Clontech), 1.6 μl dNTPs mix (2.5 mM each, PERKIN-ELMER, Foster City, Calif.), 1 μl sense primer, ZC 15,570 (SEQ ID NO:11), 1 μl antisense primer, ZC 15,575 (SEQ ID NO:12), 2 μl RediLoad (Research Genetics, Inc.), 0.4 μl 50×Advantage KlenTaq Polymerase Mix (Clontech), 25 ng of DNA from an individual hybrid clone or control and dd$H_2O$ for a total volume of 20 μl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 62° C. and 1.5 minute extension at 72° C., followed by a final 1 cycle extension of 7 minutes at 72° C. The reactions were separated by electrophoresis on a 2% agarose gel (Life Technologies, Gaithersburg, Md.).

The results showed that zfsta2 maps 2.84 cR_3000 from the framework marker WI-5113 on the chromosome 4 WICGR radiation hybrid map. Proximal and distal framework markers were WI-5113 and CHLC.GATA4C05.17, respectively. The use of surrounding markers positions zfsta2 in the 4q28.3 region on the integrated LDB chromosome 4 map (The Genetic Location Database, University of Southhampton, Www server:http://cedar.genetics.soton.ac.uk/public_html/).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A polynucleotide encoding a fusion protein comprising a secretory signal sequence having the amino acid sequence of amino acid residues 1–20 of SEQ ID NO:2, wherein said secretory signal sequence is operably linked to the amino terminal of an additional polypeptide.

* * * * *

UNITED STATES PATENT AND TRADEMARK OFFICE

CERTIFICATE OF CORRECTION

PATENT NO. : 6,355,788 B1 
DATED : March 12, 2002
INVENTOR(S) : Darrell C. Conklin and Jeff L. Ellsworth It is certified that error appears in the above-identified patent and that said Letters Patent is hereby corrected as shown below:

<u>Column 28,</u>
Line 32, the sentence beginning "zfsta2 can also be" should begin a new paragraph.

<u>Column 39,</u>
Line 7, the sentence beginning "zfsta2 polypeptide," should begin a new paragraph.

Signed and Sealed this

Twenty-fourth Day of December, 2002

JAMES E. ROGAN
*Director of the United States Patent and Trademark Office*